US012364489B2

(12) United States Patent
Gordon et al.

(10) Patent No.: US 12,364,489 B2
(45) Date of Patent: Jul. 22, 2025

(54) SYSTEM AND METHOD FOR FIXING A CRANIAL IMPLANT

(71) Applicant: THE JOHNS HOPKINS UNIVERSITY, Baltimore, MD (US)

(72) Inventors: Chad Gordon, Cockeysville, MD (US); Owen F. Friesen, Baltimore, MD (US); Cristina I. Romany, Orlando, FL (US); Nathan W. Scott, Phoenix, MD (US); Deborah I. Weidman, Bedford, MA (US); Jing Lin Cui, Baltimore, MD (US); Ku Chien Lin, Fort Lee, NJ (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 317 days.

(21) Appl. No.: 18/001,763

(22) PCT Filed: Jun. 29, 2021

(86) PCT No.: PCT/US2021/039697
§ 371 (c)(1),
(2) Date: Dec. 14, 2022

(87) PCT Pub. No.: WO2022/006163
PCT Pub. Date: Jan. 6, 2022

(65) Prior Publication Data
US 2023/0233216 A1    Jul. 27, 2023

Related U.S. Application Data

(60) Provisional application No. 63/046,165, filed on Jun. 30, 2020.

(51) Int. Cl.
*A61B 17/17*    (2006.01)
*A61B 17/16*    (2006.01)
*A61B 17/68*    (2006.01)

(52) U.S. Cl.
CPC ...... *A61B 17/1739* (2013.01); *A61B 17/1615* (2013.01); *A61B 17/1695* (2013.01); *A61B 17/688* (2013.01); *A61B 2017/1602* (2013.01)

(58) Field of Classification Search
CPC . A61B 17/16; A61B 17/1613; A61B 17/1615; A61B 17/1617; A61B 17/162;
(Continued)

(56) References Cited

U.S. PATENT DOCUMENTS 8,814,938 B2 * 8/2014 Lee ............... A61B 17/1642
                                                    623/17.11
9,277,930 B2 * 3/2016 Lee ............... A61B 17/1642
(Continued)

FOREIGN PATENT DOCUMENTS

CN      2287907 Y      8/1998
CN      202317141 U    7/2012
(Continued)

OTHER PUBLICATIONS

Belugin, M. (Authorized officer), International Search Report and Written Opinion in corresponding International Application No. PCT/US2021/039697 mailed on Sep. 16, 2021, 9 pages.
(Continued)

*Primary Examiner* — Eric S Gibson
(74) *Attorney, Agent, or Firm* — MH2 Technology Law Group LLP

(57) ABSTRACT

An attachment for a drill includes an inner housing configured to be coupled to the drill. The attachment also includes an outer housing positioned at least partially around the inner housing. The attachment also includes a vertical guide coupled to or integral with the inner housing. The attachment also includes a horizontal guide coupled to or integral with the outer housing. The attachment also includes a guide adapter configured to move along the vertical guide and the
(Continued)

horizontal guide. The inner housing and the vertical guide are configured to move vertically with respect to the outer housing and the guide adapter, and the inner housing and the guide adapter are configured to move laterally with respect to the horizontal guide and the outer housing.

20 Claims, 16 Drawing Sheets

(58) Field of Classification Search
CPC ............ A61B 17/1622; A61B 17/1624; A61B 17/1626; A61B 17/1628; A61B 17/1633; A61B 17/1635; A61B 17/1655; A61B 17/1657; A61B 17/1695; A61B 17/17; A61B 17/1703; A61B 17/1732; A61B 17/1739; A61B 17/688; A61B 2017/1602
See application file for complete search history.

(56) References Cited

U.S. PATENT DOCUMENTS

| | | | | |
|---|---|---|---|---|
| 10,653,432 | B2* | 5/2020 | Luttrell | A61B 17/151 |
| 11,957,364 | B2* | 4/2024 | Korman | A61B 17/17 |
| 12,138,131 | B2* | 11/2024 | Fares | A61C 1/12 |
| 12,150,655 | B2* | 11/2024 | Brody | A61B 5/031 |
| 2006/0089621 | A1* | 4/2006 | Fard | A61B 17/1615 |
| | | | | 606/1 |
| 2009/0216329 | A1* | 8/2009 | Lee | A61B 17/1671 |
| | | | | 623/17.11 |
| 2010/0173259 | A1* | 7/2010 | Vogel | A61C 1/084 |
| | | | | 433/72 |
| 2011/0106095 | A1* | 5/2011 | Cross | A61B 17/175 |
| | | | | 606/96 |
| 2014/0350560 | A1* | 11/2014 | Lee | A61F 2/44 |
| | | | | 606/80 |
| 2017/0000503 | A1* | 1/2017 | Keefer | A61B 17/1615 |
| 2018/0206891 | A1* | 7/2018 | Hsueh | A61B 17/7083 |
| 2020/0246101 | A1* | 8/2020 | Jones | A61B 1/0016 |
| 2022/0071736 | A1* | 3/2022 | Fares | A61C 1/14 |
| 2022/0257266 | A1* | 8/2022 | Brody | A61B 17/1695 |
| 2022/0313284 | A1* | 10/2022 | Korman | A61B 17/17 |
| 2023/0233216 | A1* | 7/2023 | Gordon | A61B 17/1739 |
| | | | | 606/281 |

FOREIGN PATENT DOCUMENTS

| | | | | |
|---|---|---|---|---|
| CN | 109512482 | A | | 3/2019 |
| CN | 112754591 | A * | 5/2021 | ............ A61B 17/16 |
| CN | 116763394 | A * | 9/2023 | |
| CN | 112754591 | B * | 11/2024 | ............ A61B 17/16 |
| RU | 2363403 | C1 | | 8/2009 |
| WO | WO-2020142767 | A1 * | 7/2020 | ............ A61C 1/082 |
| WO | WO-2021011795 | A1 * | 1/2021 | ......... A61B 17/1695 |
| WO | WO-2022006163 | A1 * | 1/2022 | ......... A61B 17/1615 |

OTHER PUBLICATIONS

Lee, S. (Authorized officer), International Preliminary Report on Patentability in corresponding International Application No. PCT/US2021/039697 mailed on Jan. 12, 2023, 8 pages.

* cited by examiner

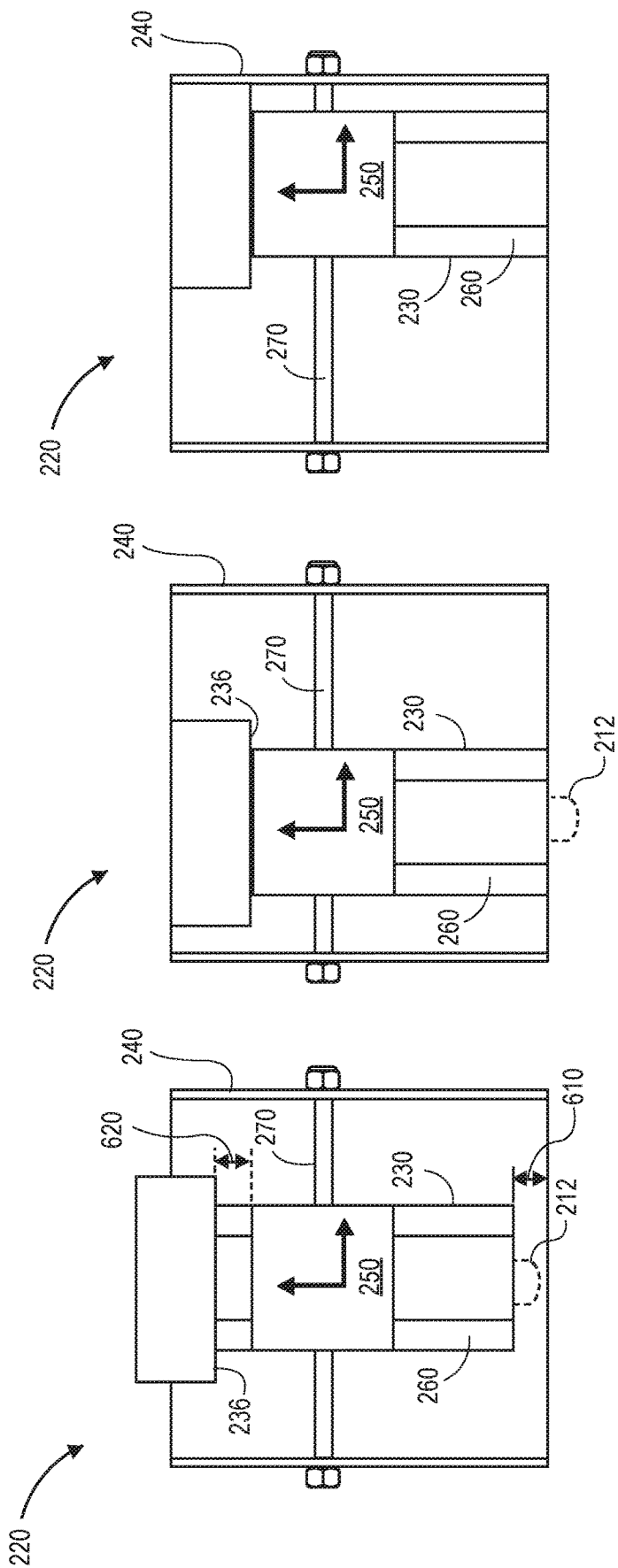

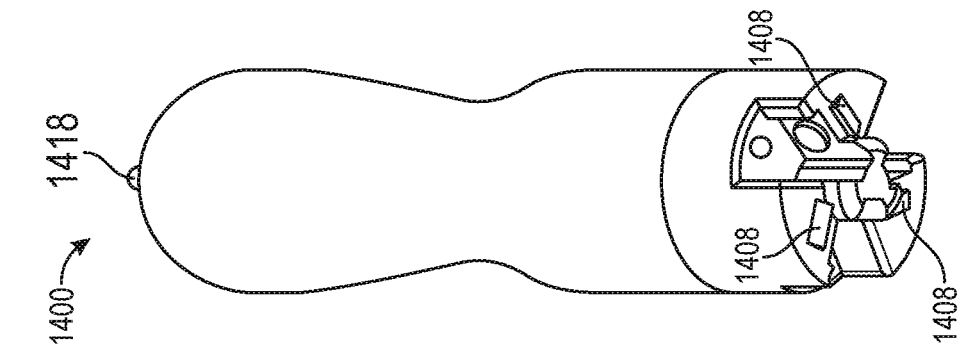
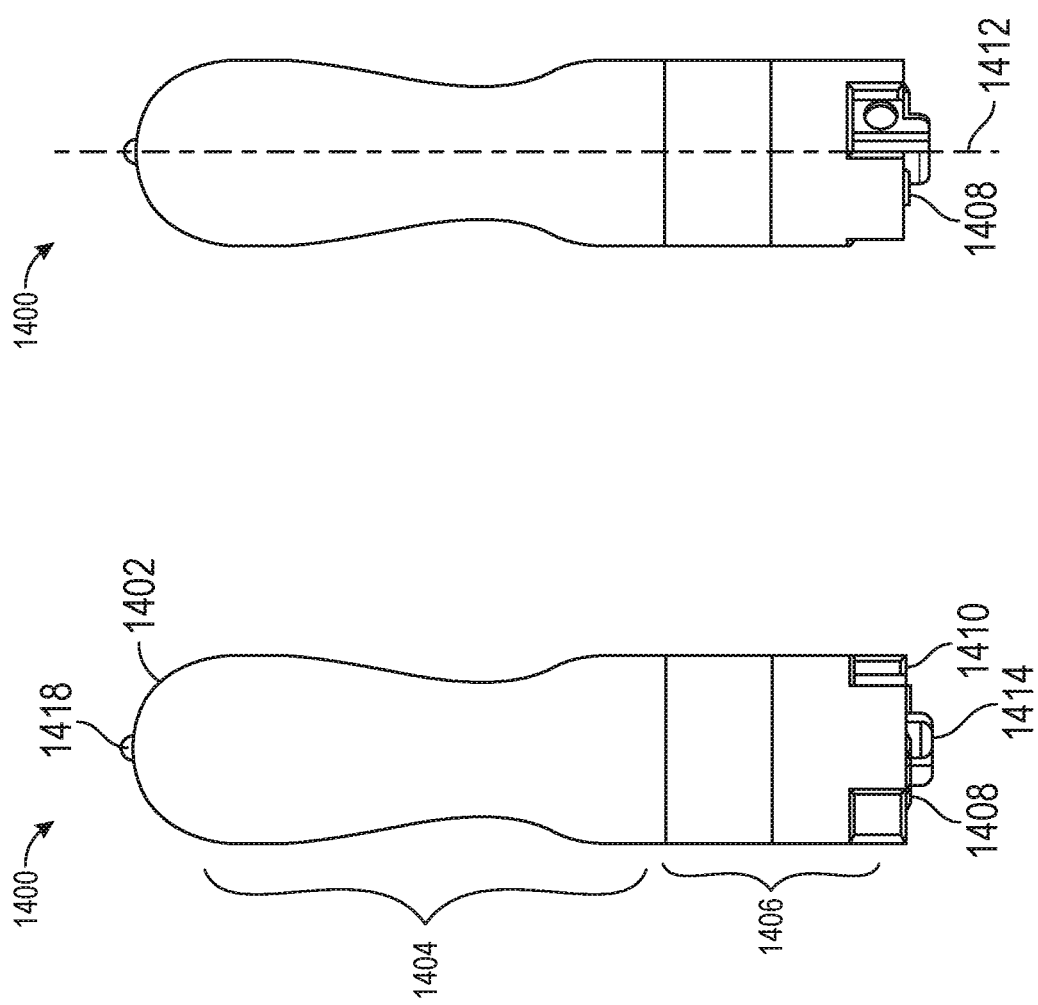

SYSTEM AND METHOD FOR FIXING A CRANIAL IMPLANT

CROSS-REFERENCE TO RELATED APPLICATIONS

This application is the national stage entry of International Patent Application No. PCT/US2021/039697, filed on Jun. 29, 2021, and published as WO 2022/006163 A1 on Jan. 6, 2022, which claims the benefit of U.S. Provisional Patent Application Ser. No. 63/046,165, filed on Jun. 30, 2020, both of which are hereby incorporated by reference herein in their entireties.

FIELD OF THE INVENTION

The present invention relates generally to systems and methods for performing a neurosurgical procedure. More particularly, the present invention relates to systems and methods for fixing a cranial implant to a skull during a neurosurgical procedure such as a craniotomy or a cranioplasty.

BACKGROUND OF THE INVENTION

Currently, when patients undergo neurosurgery, a portion of the skull (e.g., a bone flap) is removed to allow the surgeon access to the brain. At the conclusion of the operation, the surgeon may re-insert either the original bone flap, or choose to replace the bone flap with a bridge of titanium mesh or a custom implant made of alloplastic biomaterials. Regardless, each option is fixated to the surrounding skull to prevent micromotions and protect the brain underneath. Currently, to ensure rigid fixation, titanium plates and screws are used to fix the bone flap or implant at the skull's surface.

The profile of plates and screws can be visibly noticeable in areas of the skull without hair, resulting in facial asymmetry. It can also be painful to the touch in daily tasks like combing one's hair or cause localized pressure on the scalp, causing pain in patients as well as possible extrusion and post-operative complications. If the scalp opens, the patient will need to undergo another procedure as well as take antibiotics because, with the hardware exposed, the likelihood for infection is high. This is especially common in patients with extensive surgical history, those with multiple scars, and patients who have undergone chemotherapy or irradiation.

SUMMARY OF THE INVENTION

An attachment for a drill is disclosed. The attachment includes an inner housing configured to be coupled to the drill. The attachment also includes an outer housing positioned at least partially around the inner housing. The attachment also includes a vertical guide coupled to or integral with the inner housing. The attachment also includes a horizontal guide coupled to or integral with the outer housing. The attachment also includes a guide adapter configured to move along the vertical guide and the horizontal guide. The inner housing and the vertical guide are configured to move vertically with respect to the outer housing and the guide adapter, and the inner housing and the guide adapter are configured to move laterally with respect to the horizontal guide and the outer housing.

An additional attachment for a drill is also disclosed. The attachment includes an inner housing configured to be coupled to the drill and defining a bore. The drill is configured to extend through the bore such that a drill bit of the drill extends vertically-below a lower end of the inner housing by a predetermined amount. The attachment also includes an outer housing positioned at least partially around the inner housing. The attachment also includes a vertical guide coupled to or integral with the inner housing, and a horizontal guide coupled to or integral with the outer housing. The attachment also includes a guide adapter slidingly engaged with the vertical guide and the horizontal guide. The inner housing and the vertical guide are configured to slide vertically relative to the guide adapter when the drill and the inner housing move vertically with respect to the outer housing. The guide adapter is configured to slide horizontally along the horizontal guide when the drill and the inner housing move horizontally with respect to the outer housing. The attachment also includes a vertical resilient coupling operably engaged with the inner housing and the guide adapter. The vertical resilient coupling is configured to resiliently couple the inner housing and the drill with the guide adapter along a vertical axis when the inner housing and the drill move vertically with respect to the outer housing. The attachment also includes a horizontal resilient coupling operably engaged with the guide adapter and the outer housing. The horizontal resilient coupling is configured to resiliently couple the guide adapter with the outer housing along a horizontal axis when the inner housing and the drill move horizontally with respect to the outer housing.

A surgical tool is also disclosed. The surgical tool includes a drill that includes a drill bit. The surgical tool also includes an attachment configured to be coupled to the drill. The attachment includes an inner housing defining a bore. The drill is configured to extend through the bore such that the drill bit extends vertically-below a lower end of the inner housing by a predetermined amount. The attachment also includes an outer housing positioned at least partially around the inner housing. A lower end of the outer housing includes an anchoring feature. The attachment also includes a vertical guide coupled to or integral with the inner housing. The attachment also includes a horizontal guide coupled to or integral with the outer housing. The attachment also includes a guide adapter slidingly engaged with the vertical guide and the horizontal guide. The guide adapter is configured to slide vertically along the vertical guide when the drill and the inner housing move vertically with respect to the outer housing. The guide adapter is configured to slide horizontally along the horizontal guide when the drill and the inner housing move horizontally with respect to the outer housing.

An additional surgical tool is also disclosed. The surgical tool includes a drill comprising a drill bit, and a power source operably connected to the drill. The surgical tool also includes an inner housing defining a bore. The drill is configured to extend through the bore such that the drill bit extends vertically-below a lower end of the inner housing by a predetermined amount. The surgical tool also includes an outer housing positioned at least partially around the inner housing. The surgical tool also includes a vertical guide coupled to or integral with the inner housing, and a horizontal guide coupled to or integral with the outer housing. The surgical tool also includes a guide adapter slidingly engaged with the vertical guide and the horizontal guide. The inner housing and the vertical guide are configured to slide vertically relative to the guide adapter when the drill and the inner housing move vertically with respect to the outer housing. The guide adapter is configured to slide horizontally along the horizontal guide when the drill and the inner housing move horizontally with respect to the outer housing. The surgical tool also includes a vertical resilient coupling operably engaged with the inner housing and the guide adapter. The vertical resilient coupling is configured to resiliently couple the inner housing and the drill with the guide adapter along a vertical axis when the inner housing and the drill move vertically with respect to the outer housing. The surgical tool also includes a horizontal resilient coupling operably engaged with the guide adapter and the outer housing. The horizontal resilient coupling is configured to resiliently couple the guide adapter with the outer housing along a horizontal axis when the inner housing and the drill move horizontally with respect to the outer housing.

An additional surgical tool is also disclosed. The surgical tool includes a body structure that comprises a handle portion and a base portion operably connected to the handle portion. The surgical tool also includes at least one blade that extends from a lower surface of the base portion. The blade is disposed substantially perpendicular to a rotational axis of the body structure and is configured to remove biological material from a skull of a subject to create an inset of a selected depth in the skull when the blade is contacted with the skull and the body structure is manually rotated relative to the skull. The surgical tool also includes at least one protrusion that extends below the lower surface of the base portion. At least a portion of the protrusion is configured to fit within a pre-existing burr hole disposed in the skull of the subject to align the body structure and/or the blade relative to the skull when the portion of the protrusion is positioned within the pre-existing burr hole and the body structure is manually rotated relative to the skull.

A method for performing a surgical procedure is also disclosed. The method includes coupling an attachment to a drill. The attachment includes an inner housing and an outer housing. The drill includes a drill bit. The method also includes contacting a skull with the outer housing. The method also includes moving the drill and the inner housing downward with respect to the outer housing and the skull. The method also includes moving the drill and the inner housing laterally with respect to the outer housing and the skull to cause the drill bit to form a slot in the skull.

Another method for performing a surgical procedure is also disclosed. The method includes contacting a skull with an outer housing of a surgical tool in which the surgical tool comprises an inner housing, the outer housing, and a drill that comprises a drill bit. The method also includes moving the drill and the inner housing downward with respect to the outer housing and the skull. The method also includes moving the drill and the inner housing laterally with respect to the outer housing and the skull to cause the drill bit to form a slot in the skull.

Another method for performing a surgical procedure is also disclosed. The method includes positioning at least a portion of a protrusion of a surgical tool within a burr hole disposed in a skull. The surgical tool comprises a body structure that comprises a handle portion and a base portion operably connected to the handle portion, a blade that extends from at least a first lower surface of the base portion, and the protrusion in which the protrusion extends below the first lower surface of the base portion. The method also includes manually rotating the body structure relative to the skull to cause the blade to form a slot in the skull.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIG. 6A illustrates a side, cross-sectional view of the attachment in a first state, according to an embodiment.

FIG. 6B illustrates a side, cross-sectional view of the attachment in a second state, according to an embodiment.

FIG. 6C illustrates another side, cross-sectional view of the attachment in the second state, according to an embodiment.

FIG. 14A illustrates a schematic side view of an example of another surgical tool, according to an embodiment.

FIG. 14B illustrates another schematic side view of the surgical tool depicted in FIG. 14A.

FIG. 14C illustrates a schematic perspective view of the surgical tool depicted in FIG. 14A.

DETAILED DESCRIPTION

Figure 1A:
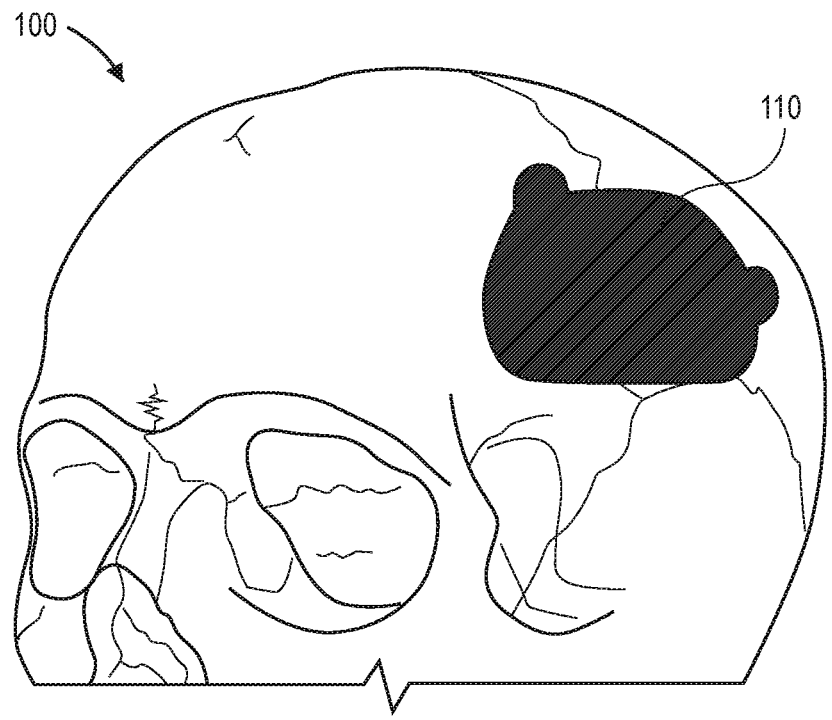
FIG. 1A illustrates a schematic perspective view of a skull with a defect therein resulting from the removal of a bone flap during neurosurgery (e.g., a craniotomy procedure), according to an embodiment.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The systems and methods disclosed herein include a surgical tool that is configured to create a linear, depth-controlled, recessed slot in the skull, bone flap, and/or implant such that the plates and screws used in the affixation process are substantially flush with the outer surface of the skull. This reduces the profile when compared to the current fixation method.

Surgical drills may include four components: the console, the drill, the attachment(s), the drill bit(s). Currently, the attachments are fixed to the drill by a user (e.g., a scrub technician) who then locks a drill bit to the attachment. The systems and methods disclosed herein modify the attachments and the drill bits such that the attachment is extended to provide a safety or a control in creating the inset. The housing of the attachment may be compatible with the installment of surgical drill bits by scrub techs as well as visibility and irrigation during usage.

At the start of the craniotomy procedure, the surgeon may use the attachment in a first (e.g., plunge) mode in which the surgeon sets the drill in the desired position, pushes in the inner component with the bit, and passes it along the curvature of the skull. This is done before the bone flap is removed and results in a sort of jigsaw puzzle for re-fitting the bone flap at the end of the procedure. The attachment may prevent the bit from removing bone below a predetermined depth as well as follow the skull's curvature. The material removal is comparable to milling the surface of a material or using a planar device in woodworking. To achieve this, a surgical burr bit (e.g. barrel burr) can be used in a lateral motion.

Once the bone flap is removed, there is a step (e.g., a ledge) between the dura and the skull surface. The surgeon may utilize that step at the dura-skull interface (e.g., in the recessed area) as a starting point for the creation of a recessed slot in cranioplasty procedures. The surgeon may place the lip of the attachment at this stepping point and move the bit across the surface of the skull. The same type of procedure can be done on the bone flap or implant and then the plates can be installed (e.g., screwed into place) such that they are flush with the surface on both sides of the implant-bone interface.

FIG. 1A illustrates a schematic perspective view of a skull 100 with a defect 110 resulting from the removal of a bone flap during neurosurgery (e.g., a craniotomy procedure), according to an embodiment. After a patient undergoes a craniotomy, a procedure that opens the scalp to access the skull 100, dura, and brain for surgical treatment, the surgeon may re-use the original bone flap if it is not deformed. The bone flap is the piece of skull 100 that surgeons drill and remove to create the defect 110 (e.g., an opening), which provides access the brain.

The surgeon may perform the craniotomy on the temporal side of the skull 100 for two reasons: aesthetic outcomes and ease of access to the brain during the procedure. If the bone flap is deformed or unsuitable to place back into the skull 100, a titanium mesh or a custom implant made of alloplastic biomaterials can be used to provide a cross sectional fill to the resected area and protect the brain.

Figure 1B:
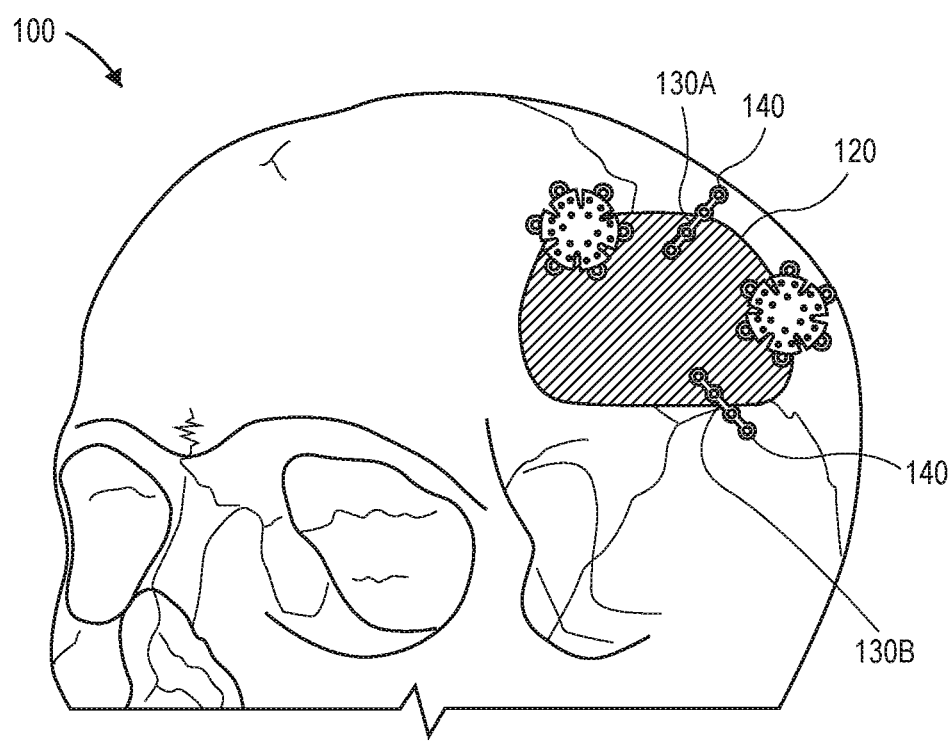
FIG. 1B illustrates a schematic perspective view of the skull with the bone flap (or an implant) positioned at least partially within the defect, according to an embodiment.

FIG. 1B illustrates a schematic perspective view of the skull 100 with a bone flap (or an implant) 120 positioned at least partially within the defect 110, according to an embodiment. Reference number 120 will refer to the bone flap and/or the implant herein. In one embodiment, the bone flap 120 may be inserted back into the defect 110 to complete the surgery. In another embodiment, when the surgeon determines that the bone flap 120 is unsuitable to be placed back into the skull 100, the surgeon may then suture the scalp back together after the procedure and sometimes install a temporary titanium mesh. The hospital staff may then perform a computed tomography (CT) scan of the head to get the exact dimensions of the defect 110. A custom-made laser cut poly methyl methacrylate (PMMA) implant 120 may then be produced for insertion into the patient's skull 100 through a cranioplasty procedure. A cranioplasty procedure is where the surgeon performs a craniotomy to repair skull 100 defects for aesthetic outcomes. The implant 120 may have substantially the same size and shape as the bone flap 120.

The current, most widely-used method of cranial implant affixation, to secure the implant 120 to be level with the rest of the skull 100, is using (e.g., titanium) plates 130A, 130B and screws 140 over top of the interface between bone 100 and implant 120. Surgeons screw in titanium screws 140 through holes in the plates 130A, 130B to affix the bone flap (or implant) 120 to the skull 100.

The surgeon may pre-plate the implant 120 to ensure that the plates 130A, 130B are secured and in the desired locations. The plates 130A, 130B can be spaced a couple of inches apart. The PMMA implants 120 may be at least 1 mm in thickness (by FDA standards). The titanium plate thickness may range from about 0.25 mm to about 1.0 mm (e.g., about 0.4 mm, about 0.6 mm, or about 0.8 mm), and the screws 140 are about 4 mm in length. The surface profile of the screws 140 may have some offset provided by a countersink.

As mentioned above, patients can experience pain from the conventional fixation method because of the raised profile created by the titanium plates 130A, 130B and screws 140. Although to the naked eye, the raised profile of the plates 130A, 130B and screws 140 looks insignificant (e.g., the profile is less than or equal to about 1 mm), it is enough to cause pain for the patients and is often noticeable through the scalp in areas absent hair post-surgery. This pain is caused by the contact between the subcutaneous tissue and the plates 130A, 130B and screws 140.

Figure 2A:
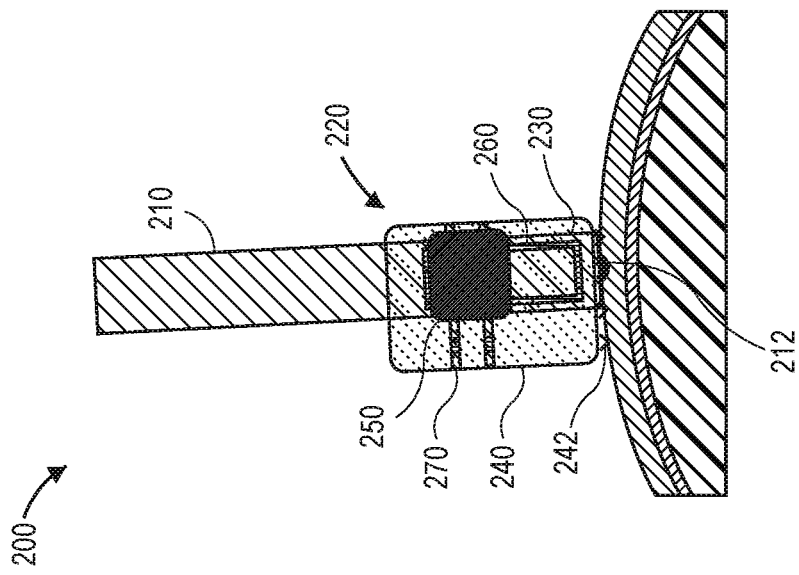
FIGS. 2A-2C illustrate side schematic views of a surgical tool, according to an embodiment.
Figure 2B:
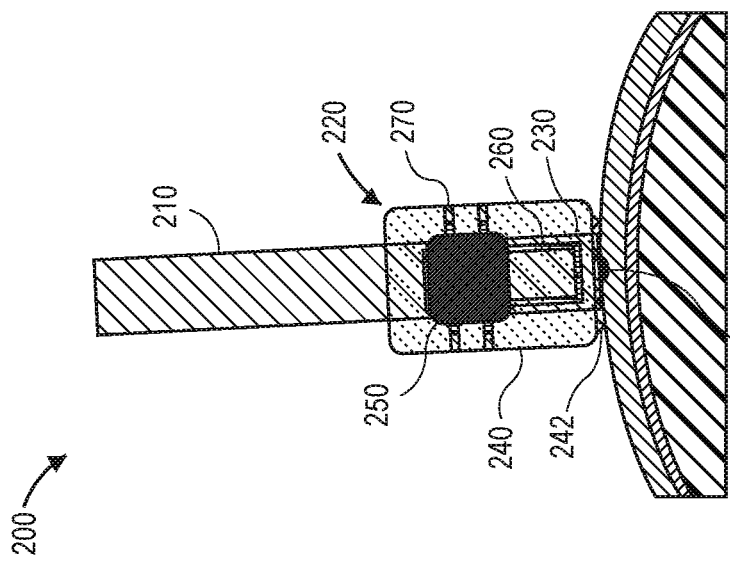
Figure 2C:
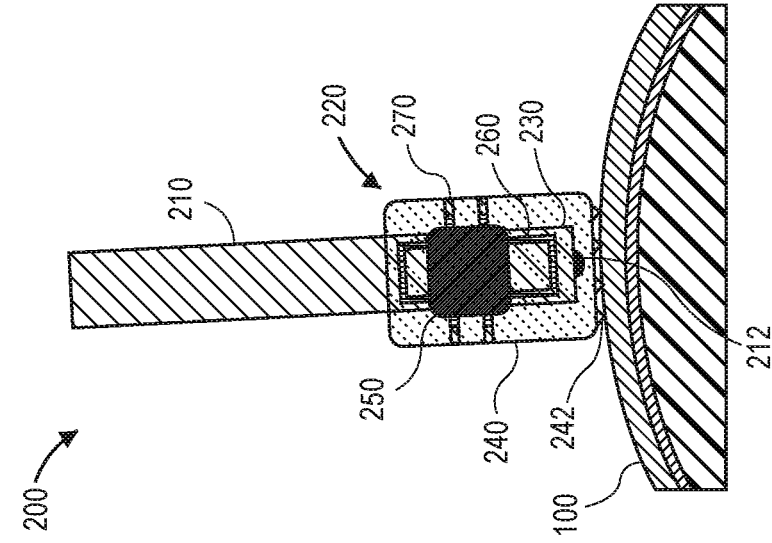

FIGS. 2A-2C illustrate side schematic views of a surgical tool 200, according to an embodiment. As described below, the surgical tool 200 may be configured to form a slot in the skull 100, the bone flap 120, and/or the implant 120. The plates 130A, 130B and screws 140 may be positioned in the slot so that the plates 130A, 130B and screws 140 do not protrude outward from the outer surface of the skull 100.

The surgical tool 200 may include a drill (e.g., a DREMEL®, a craniotomy drill, neurosurgical drill, etc.) 210 including a drill bit 212. The surgical tool 200 may also include an attachment 220 that may be attached/coupled to the surgical drill 210. The attachment 220 may include an inner housing 230, an outer housing 240, a guide adapter 250, a vertical guide 260, and a horizontal guide 270.

The inner housing 230 may be coupled to the drill 210 such that the drill bit 212 extends outward (e.g., downward) from the lower end of the inner housing 230 by a predetermined amount. The predetermined amount may be selected by the surgeon and may be from about 0.5 mm to about 8 mm, about 0.5 mm to about 1 mm, about 1 mm to about 3 mm, or about 3 mm to about 8 mm. The predetermined amount may determine the depth of the slot formed in the skull 100, the bone flap 120, and/or the implant 120 by the drill bit 212.

The outer housing 240 may be positioned outward from (e.g., at least partially around) the inner housing 230. The outer housing 240 may include one or more anchoring features 242 in/on a lower surface thereof that are configured to temporarily secure the outer housing 240 in place with respect to the skull 100. The anchoring feature(s) 242 may be or include teeth, grit, adhesive, or other surface treatments that are configured to temporarily secure the outer housing 240 in place with respect to the skull 100. As shown in FIG. 2A, when the tool 200 is in a first state, the drill bit 212 may be positioned within the outer housing 240. Said another way, the drill bit 212 may not extend outward (e.g., downward) from the lower end of the outer housing 240. As a result, the drill bit 212 may not drill into the skull 100.

The inner and outer housings 230, 240 may be coupled together via the guide adapter 250, the vertical guide 260, the horizontal guide 270, or a combination thereof. The drill 210 and the inner housing 230 may be configured to move with respect to the outer housing 240. For example, as shown in FIG. 2B, the guide adapter 250 and/or the vertical guide 260 may enable the drill 210 and the inner housing 230 to move vertically (e.g., upward and downward) with respect to the outer housing 240. This may allow the drill bit 212 to contact (e.g., plunge into) the skull 100 a predetermined distance (e.g., the distance that the drill bit 212 protrudes from the inner housing 230).

As shown in FIG. 2C, the guide adapter 250 and/or the horizontal guide 270 may enable the drill 210 and the inner housing 230 to move laterally (e.g., side-to-side) with respect to the outer housing 240. Once the drill bit 212 is plunged into the skull 100, the lateral movement may allow the drill bit 212 to form a linear slot in the skull 100. The length of the slot may be limited by the inner housing 230 contacting the (e.g., stationary) outer housing 240, as shown in FIG. 2C.

Figure 3:
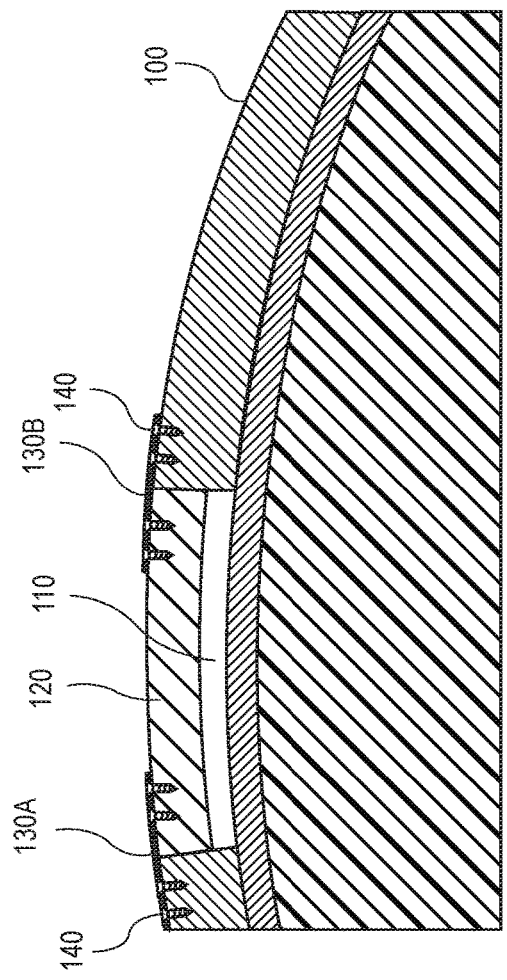
FIG. 3 illustrates a schematic cross-sectional view of a portion of the skull, with the bone flap (or the implant) positioned within the defect and fixed in place with plates and screws, according to an embodiment.

FIG. 3 illustrates a schematic cross-sectional view of a portion of the skull 100, with the bone flap and/or implant 120 positioned within the defect 110 and fixed in place with the plates 130A, 130B and the screws 140, according to an embodiment. FIG. 4A illustrates an enlarged view of a portion of FIG. 3. As may be seen in FIGS. 3 and 4A, the plate 130A and the screws 140 protrude upward/outward from the skull 100 and the bone flap and/or implant 120 (e.g., by about 1 mm), which may cause the problems discussed above.

Figure 4B:
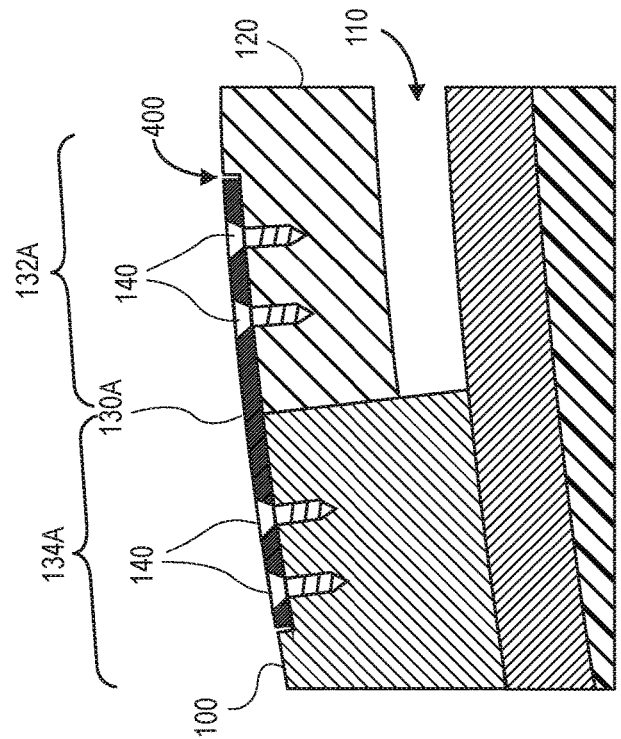
FIG. 4B illustrates a schematic cross-sectional view similar to that in FIG. 4A, but with the plate and screws positioned within a slot formed by the surgical tool, according to an embodiment.
Figure 4A:
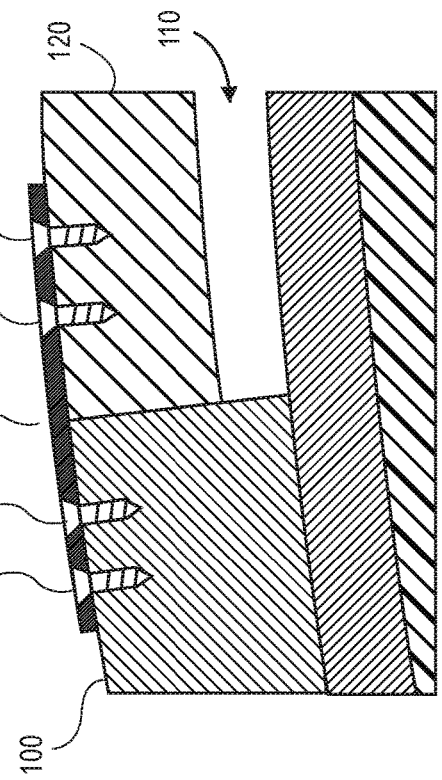
FIG. 4A illustrates an enlarged view of a portion of FIG. 3.

FIG. 4B illustrates a schematic cross-sectional view similar to that in FIG. 4A, but with the plate 130A and screws 140 positioned within a slot 400 formed by the surgical tool 200, according to an embodiment. As may be seen in FIG. 4B, the tool 200 has formed the slot 400 in the skull 100 and the bone flap and/or implant 120. More particularly, a first portion (e.g., a first half/side) of the slot 400 may be formed in the bone flap and/or implant 120, and a second portion (e.g., a second half/side) of the slot 400 may be formed in a remainder of the skull 100.

The plate 130A and/or the screws 140 may be positioned within the slot 400. More particularly, a first portion (e.g., a first half/side) 132A of the plate 130A may be positioned within the corresponding first portion of the slot 400 in the bone flap and/or implant 120, and a second portion (e.g., a second half/side) 134A of the plate 130A may be positioned within the corresponding second portion of the slot 400 in the skull 100.

As a result, the outer surfaces of the plate 130A and/or the screws 140 may protrude upward/outward from the outer surfaces of the skull 100 and/or the bone flap/implant 120 by less than about 1 mm, less than about 500 μm, less than about 100 μm, or less than about 10 μm. In another example, the outer surfaces of the plate 130A and/or screws 140 may be substantially flush with the outer surfaces of the skull 100 and/or the bone flap/implant 120. In yet another example, the outer surfaces of the plate 130A and/or screws 140 may be recessed with respect to (e.g., positioned below) the outer surfaces of the skull 100 and/or the bone flap/implant 120.

Figure 5:
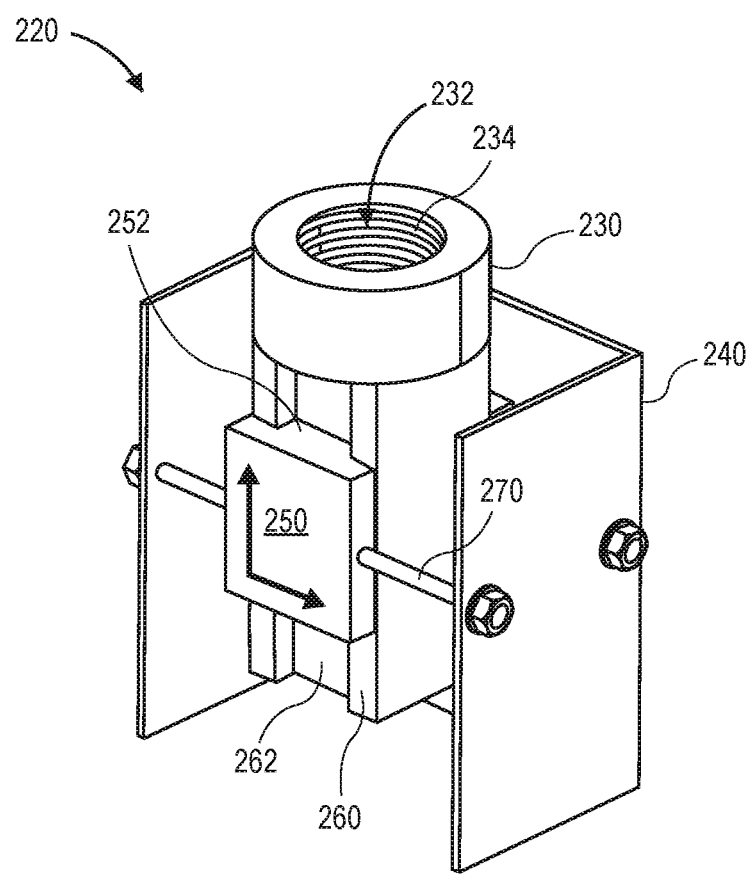
FIG. 5 illustrates a schematic view of one embodiment of the attachment (with a portion of an outer housing removed to better show the internal components), according to an embodiment.

FIG. 5 illustrates a schematic view of one embodiment of the attachment 220 (with a portion of the outer housing 240 removed to better show the internal components), according to an embodiment. As may be seen, the inner housing 230 may define a vertical axial bore 232 through which the drill 210 may extend. The inner surface of the inner housing 230 may define inner threads 234 which may engage outer threads of the drill 210 to couple the drill 210 and the inner housing 230 together.

The inner housing 230 may include the vertical guide 260. The vertical guide 260 may be or include one or more vertical tracks that are coupled to or integral with the outer surface of the inner housing 230. As shown, the vertical guide 260 may include first and second portions that are positioned on opposing sides of the inner housing 230.

The guide adapter 250 may be engaged with the vertical guide 260. As shown, the guide adapter 250 may include first and second portions that are engaged with the first and second portions of the vertical guide 260, respectively. In the embodiment shown, each portion of the vertical guide 260 may include a recess 262, and each portion of the guide adapter 250 may include a protrusion 252 that is positioned at least partially within the recess 262. The protrusion 252 may be configured to move (e.g., slide) vertically within the recess 262. This may allow the inner housing 230 (and the drill 210 coupled thereto) to move up and down with respect to the (e.g., vertically-stationary) outer housing 240 and/or guide adapter 250. More particularly, the inner housing 230 (and the drill 210 coupled thereto) may be moved downward to plunge the drill bit 212 into the skull 100 and/or the implant 120, and may be moved upward to withdraw the drill bit 212 from the skull 100 and/or the implant 120. In another embodiment, vertical guide 260 may include a protrusion, and the guide adapter 250 may include a recess.

The horizontal guide 270 may be coupled to the outer housing 240 and/or the guide adapter 250. As shown, the horizontal guide 270 may include first and second portions that are coupled to the first and second portions of the guide adapter 250. Each portion of the horizontal guide 270 may be or include a horizontal rod (e.g., shaft) having opposing ends that are coupled to opposing walls of the outer housing 240. The first and second portions of the horizontal guide 270 may be substantially parallel to one another.

FIG. 6A illustrates a side, cross-sectional view of the attachment 220 in a first (e.g., non-plunging) state, according to an embodiment. In the first position, a gap 610 exists between the bottom of the inner and outer housings 230, 240. When the drill 210 is coupled to the inner housing 230, this gap 610 may be greater than or equal to the length that the drill bit 212 (shown in dashed lines) protrudes from the inner housing 230, such that the drill bit 212 does not protrude below the lower end of the outer housing 240. As such, when the adapter 220 is in the first state, the outer housing 240 prevents the drill bit 212 from cutting (e.g., plunging into the skull 100). In addition, when the attachment 220 is in the first state, another gap 620 may exist between a shoulder 236 of the inner housing 230 and the upper end of the guide adapter 250. The gaps 610, 620 may have substantially the same vertical lengths.

FIG. 6B illustrates a side, cross-sectional view of the attachment 220 in a second (e.g., plunging) state, according to an embodiment. To transition from the first state to the second state, the inner housing 230 may move downward with respect to the outer housing 240 and the guide adapter 250. The downward movement is stopped when the shoulder 236 of the inner housing 230 contacts the upper end of the guide adapter 250. As may be seen, in the second state, the first and second gaps 610, 620 are no longer present. As such, when the adapter 220 is in the second state, the lower ends of the inner and outer housings 230, 240 may be substantially aligned. As a result, the drill bit 212 (shown in dashed lines) may protrude below the lower ends of the inner and outer housings 230, 240 and be ready to cut (e.g., plunge into the skull 100). In addition, FIG. 6B shows the inner housing 230 and the guide adapter 250 moved laterally to the left. For example, the guide adapter 250 may move laterally to the left along the horizontal guide 270.

FIG. 6C illustrates another side, cross-sectional view of the attachment 220 in the second (e.g., plunging) state, according to an embodiment. In FIG. 6C, the inner housing 230 and the guide adapter 250 have moved laterally to the right. For example, the guide adapter 250 may move laterally to the right with respect to (e.g., along) the horizontal guide 270. As mentioned above, once the drill bit 212 is plunged into the skull 100 (or the implant 120), the lateral movement may extend the length of the slot 400.

Figure 7A:
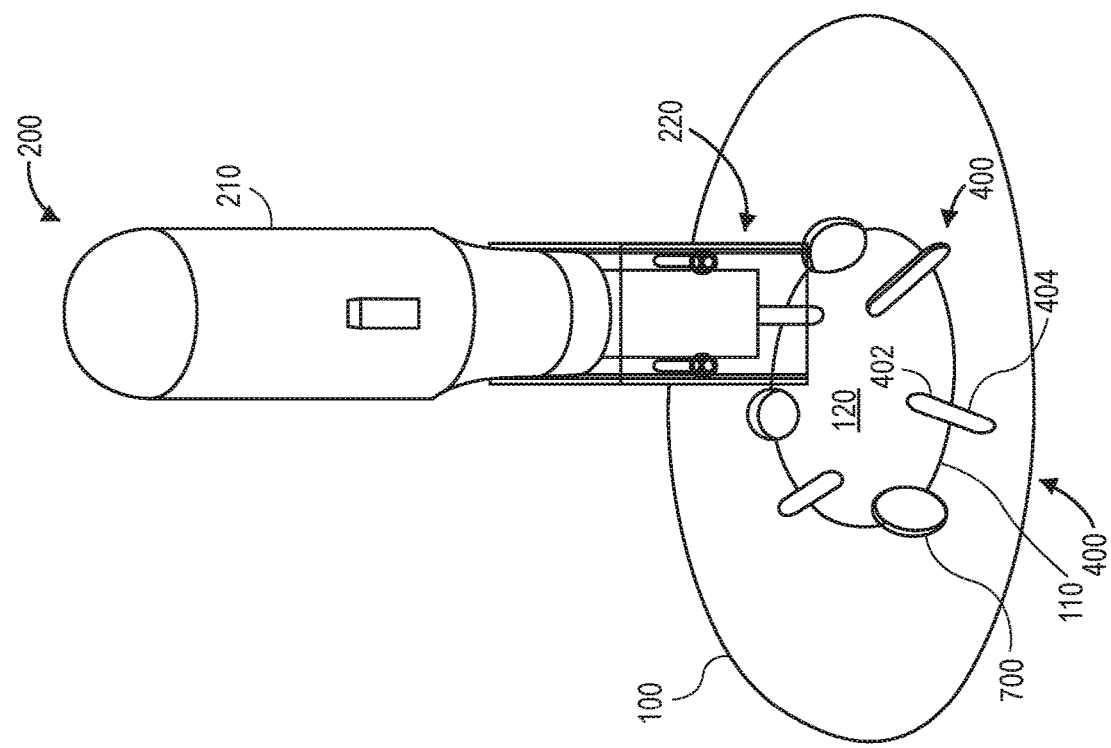
FIGS. 7A and 7B illustrate perspective views of the surgical tool forming slots in the skull and the bone flap (or the implant), according to an embodiment.
Figure 7B:
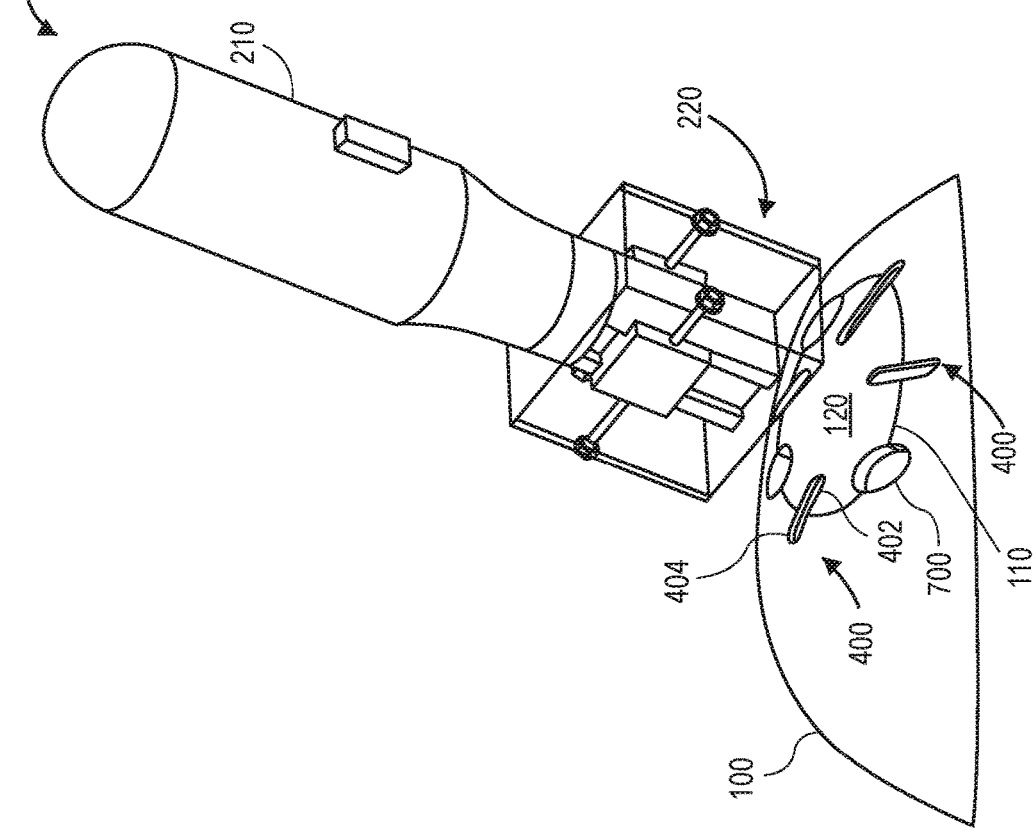

FIGS. 7A and 7B illustrate perspective views of the surgical tool 200 forming slots 400 in the skull 100 and the bone flap/implant 120, according to an embodiment. As mentioned above, a first portion 402 of each slot 400 may be formed in the bone flap and/or the implant 120. A second portion 404 of each slot 400 may be formed in the remainder of the skull 100. In this manner, the first portion 132A of each plate 130A, 130B may be positioned in the corresponding first portion 402 of the slot 400 that is formed in the bone flap and/or implant 120, and the second portion 134A of each plate 130A, 130B may be positioned in the corresponding second portion 404 of the slot 400 that is formed in the skull 100.

FIGS. 7A and 7B also show one or more (e.g., burr) holes 700 formed in the skull 100. The burr holes 700 may relieve cranial pressure. The burr holes 700 may also or instead facilitate aligning the bone flap and/or implant 120 toward the end of the surgery.

Figure 8B:
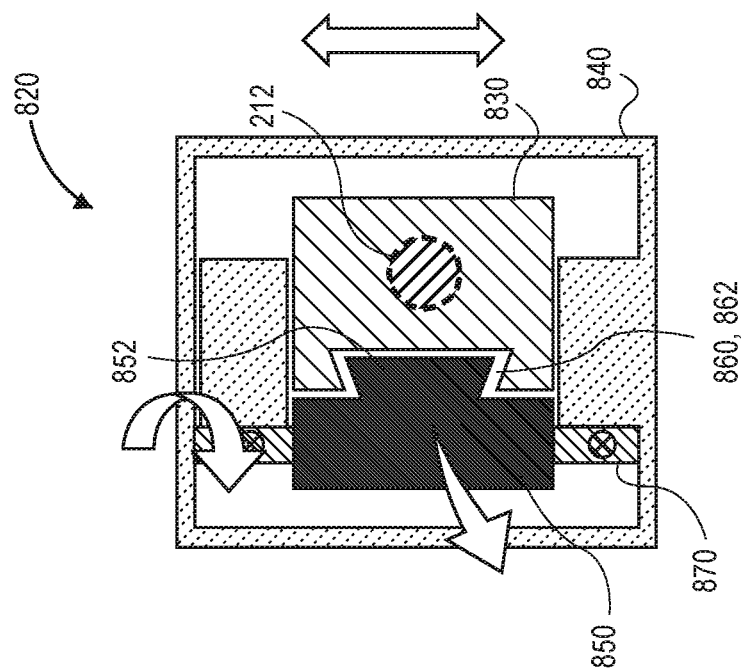
FIG. 8B illustrates a top view of the attachment, according to an embodiment.
Figure 8A:
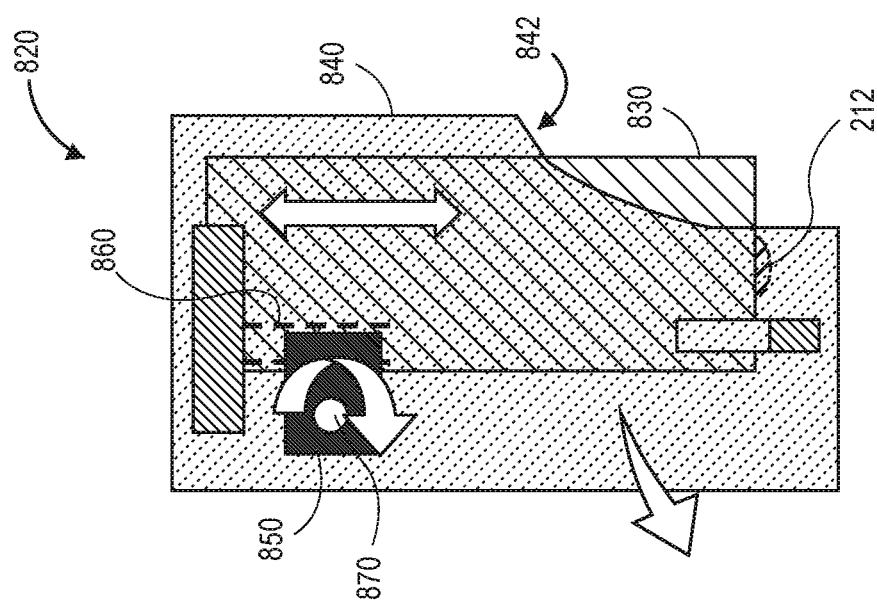
FIG. 8A illustrates a side view of an example of another attachment in a first state, according to an embodiment.

FIG. 8A illustrates a side view of another embodiment of an attachment 820 in a first (e.g., non-plunging) state, according to an embodiment. The attachment 820 may be similar to the attachment 220. For example, the attachment 820 may include an inner housing 830, an outer housing 840, a guide adapter 850, a vertical guide 860, and a horizontal guide 870.

The inner housing 830 may be configured to have the drill 210 extend therethrough. While the drill 210 is not shown in FIG. 8, the drill bit 212 is shown in dashed lines. The drill bit 212 may extend below the lower end of the inner housing 830 by the predetermined amount, which is the depth that the slot 400 will be.

The outer housing 840 may include a window 842. The window 842 may extend from the lower end of the outer housing 840 upward from about 30% to about 70% or about 40% to about 60% of the height of the outer housing 840. The window 842 may extend around about 25% to about 75% or about 30% to about 60% of the perimeter of the outer housing 840. As described below, the window 842 may facilitate a rocking function of the attachment 820.

FIG. 8B illustrates a top view of the attachment 820, according to an embodiment. The inner housing 830 may include the vertical guide 860. The vertical guide 860 may be or include one or more vertical tracks that are coupled to or integral with the outer surface of the inner housing 830. The guide adapter 850 may be engaged with the vertical guide 860. The vertical guide 860 may include a recess 862, and the guide adapter 850 may include a protrusion 852 that is positioned at least partially within the recess 862. The protrusion 852 may be configured to move (e.g., slide) vertically within the recess 862. This may allow the inner housing 830 (and the drill 210 coupled thereto) to move up and down with respect to the (e.g., vertically-stationary) outer housing 840 and guide adapter 850. More particularly, the inner housing 830 (and the drill 210 coupled thereto) may be moved downward to plunge the drill bit 212 into the skull 100 and/or the implant 120, and may be moved upward to withdraw the drill bit 212 from the skull 100 and/or the implant 120. In another embodiment, vertical guide 860 may include a protrusion, and the guide adapter 850 may include a recess.

The horizontal guide 870 may be coupled to the outer housing 840 and/or the guide adapter 850. The horizontal guide 870 may be or include a horizontal rod (e.g., shaft) having opposing ends that are coupled to opposing walls of the outer housing 840.

Figure 9:
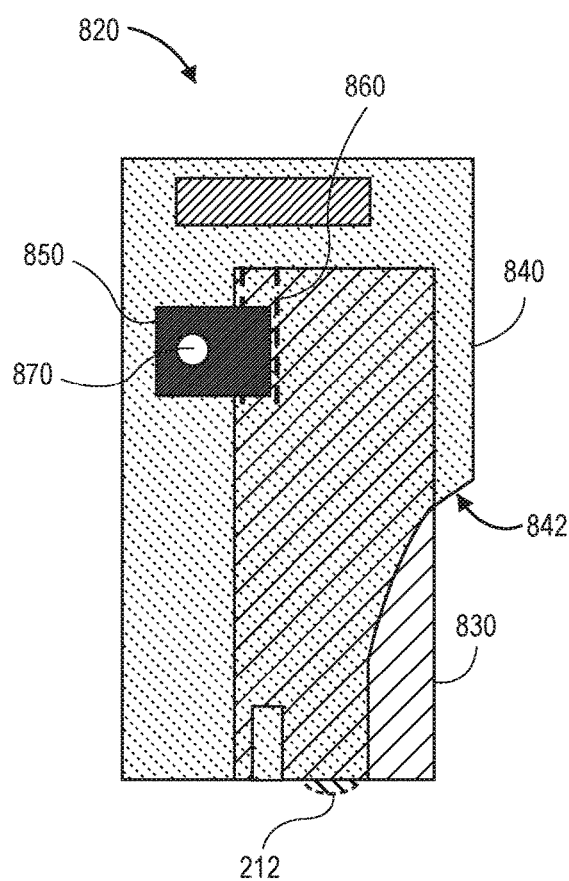
FIG. 9 illustrates another side view of the attachment in a second state, according to an embodiment.

FIG. 9 illustrates another side view of the attachment 820 in a second (e.g., plunging) state, according to an embodiment. To transition from the first state to the second state, the inner housing 830 may move downward with respect to the outer housing 840 and the guide 850. When the adapter 820 is in the second state, the lower ends of the inner and outer housings 830, 840 may be substantially aligned. As a result, the drill bit 212 (shown in dashed lines) may protrude below the lower ends of the inner and outer housings 830, 840 and be ready to cut (e.g., plunge into the skull 100).

Figure 10:
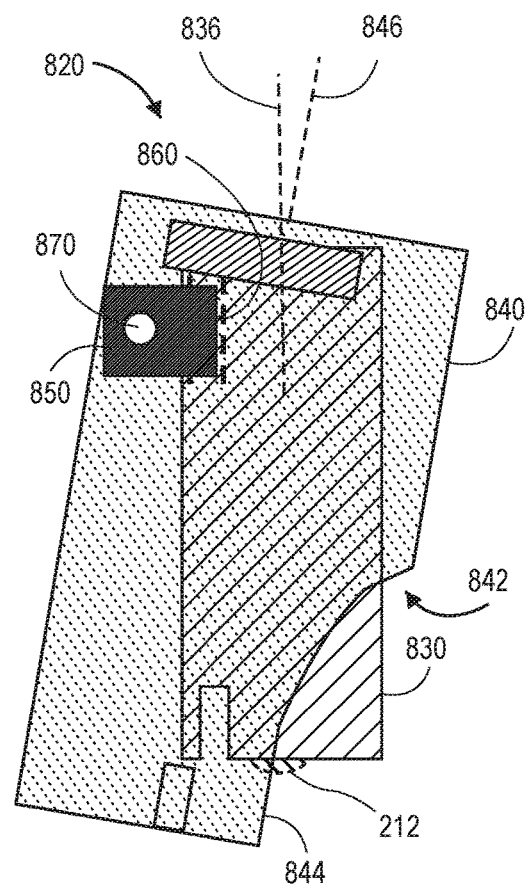
FIG. 10 illustrates another side view of the attachment in a third state, according to an embodiment.

FIG. 10 illustrates another side view of the attachment 820 in a third (e.g., rocking) state, according to an embodiment. The attachment 820 may be configured to rock when the attachment 820 is in the non-plunging state and/or the plunging state. In FIGS. 8 and 9, a central longitudinal axis 836 through the drill 210 and the inner housing 830 is substantially aligned (e.g., coaxial) with a central longitudinal axis 846 through the outer housing 840. However, when the attachment 220 is rocking, as shown in FIG. 10, the axes 836, 846 are no longer aligned. For example, the drill 210 and the inner housing 830 may pivot with respect to the outer housing 840 such that an angle between the axes 836, 846 is from about 5° to about 45°, about 5° to about 15°, about 15° to about 30°, or about 30° to about 45°. The inner housing 830 may be positioned at least partially within the window 842 when the attachment 820 is in the rocking state.

In at least one embodiment, the attachment 820 may be positioned such that an edge 844 of the outer housing 840 that defines the window 842 contacts an edge of the skull 100 that defines the defect 110. The attachment 820 may then rock (i.e., the angle between the axes 836, 846 may increase), which may allow the length of the slot 400 to be increased along the curvature of the skull 100.

FIGS. 13A-G illustrate schematic views of an example of another attachment or aspects thereof, according to an embodiment. As shown, attachment 1300 includes inner housing 1302 configured to be coupled to a drill (not included in the views shown) and defining a bore. The drill (e.g., a DREMEL®) is configured to extend through the bore such that drill bit 1303 of the drill extends vertically-below a lower end of inner housing 1302 by a predetermined amount selected by the surgeon and may be from about 0.5 mm to about 8 mm, about 0.5 mm to about 1 mm, about 1 mm to about 3 mm, or about 3 mm to about 8 mm, in some embodiments. Attachment 1300 is configured to remove biological material (e.g., bone fragments) from the skulls of subjects to create insets of selected depths in the skulls to receive, for example, plates and screws as described herein. Attachment 1300 also includes outer housing 1304 positioned at least partially around inner housing 1302. Various inset or slot shapes can be created using the attachments and surgical tools disclosed herein. In some embodiments, for example, insets comprise cross-sectional shapes, such as circles, ovals, squares, rectangles, triangles, or the like. In some embodiments, inner housings, outer housings, and drills are fabricated as inseparable components of a given surgical tool.

Attachment 1300 also includes vertical guide 1305 coupled to or integral with inner housing 1302, and horizontal guide 1307 coupled to or integral with outer housing 1304. As shown, attachment 1300 also includes guide adapter 1308 slidingly engaged with vertical guide 1305 and horizontal guide 1307. Inner housing 1302 and vertical guide 1305 are configured to slide vertically relative to guide adapter 1308 when the drill and inner housing 1302 move vertically with respect to outer housing 1304 (see, e.g., FIGS. 13 E and F). Guide adapter 1308 is configured to slide horizontally along horizontal guide 1307 when the drill and inner housing 1302 move horizontally with respect to outer housing 1304 (see, e.g., FIGS. 13 G and H).

As further shown, attachment 1300 also includes vertical resilient coupling 1306 operably engaged with inner housing 1302 and guide adapter 1308. Vertical resilient coupling 1306 (shown as a spring) is configured to resiliently couple inner housing 1302 and the drill with guide adapter 1308 along vertical axis 1309 when inner housing 1302 and the drill move vertically with respect to outer housing 1304. Attachment 1300 also includes horizontal resilient coupling 1310 (shown as a spring) operably engaged with guide adapter 1308 and outer housing 1304. Horizontal resilient coupling 1310 is configured to resiliently couple guide adapter 1308 with outer housing 1304 along horizontal axis 1311 when inner housing 1302 and the drill move horizontally with respect to outer housing 1304. Various resilient couplings are optionally adapted for use in the attachments and surgical tools disclosed herein, including springs, elastomeric materials, and hydraulic pistons (e.g., miniature hydraulic pistons or shocks), among other such couplings.

FIGS. 14A-G illustrate schematic views of an example of another surgical tool or portions thereof, according to an embodiment. As shown, surgical tool 1400 includes body structure 1402 that comprises handle portion 1404 and base portion 1406 operably connected to handle portion 1404. Surgical tool 1400 also includes blades 1408 that extend from lower surface 1410 of base portion 1406. Blades 1408 are typically disposed substantially perpendicular to rotational axis 1412 of body structure 1402 and are configured to remove biological material from a skull of a subject to create an inset of a selected depth in the skull when blades 1408 are contacted with the skull and body structure 1402 is manually rotated relative to the skull. In some embodiments, only one blade is included in a given surgical tool, whereas in other embodiments, at least two blades, at least three blades (as shown), or more blades that extend from lower surfaces of base portions. Surgical tool 1400 also includes protrusion 1414 that extends below lower surface 1410 of base portion 1406. At least a portion of protrusion 1414 is configured to fit within a pre-existing burr hole disposed in the skull of the subject to align body structure 1402 and/or blades 1408 relative to the skull when the portion of protrusion 1414 is positioned within the pre-existing burr hole and body structure 1402 is manually rotated relative to the skull. As additionally shown, surgical tool 1400 also includes at least one recessed area 1416 disposed in base portion 1406. Recessed area 1416 is configured to receive the biological material removed from the skull of the subject when blades 1408 are contacted with the skull and body structure 1402 is manually rotated relative to the skull.

In some embodiments, surgical tool 1400 further includes a power source (not within view) operably connected to the surgical tool, and feedback mechanism 1418 (shown as a light source (e.g., an LED light) to provide a visual feedback signal and sensor 1417 (e.g., a pressure sensor, a contact sensor, etc.)) operably connected at least to the power source (e.g., a battery, etc.). The feedback mechanism is configured to provide a feedback signal to a user (e.g., a surgeon) of the surgical tool when blades 1408 reach the selected depth in the skull of the subject during use of the surgical tool. In other exemplary embodiments, feedback mechanisms include one or more speakers that provide auditory feedback signals. Optionally, feedback mechanisms are adapted for use with any of the other attachments or surgical tools disclosed herein.

Figure 11:
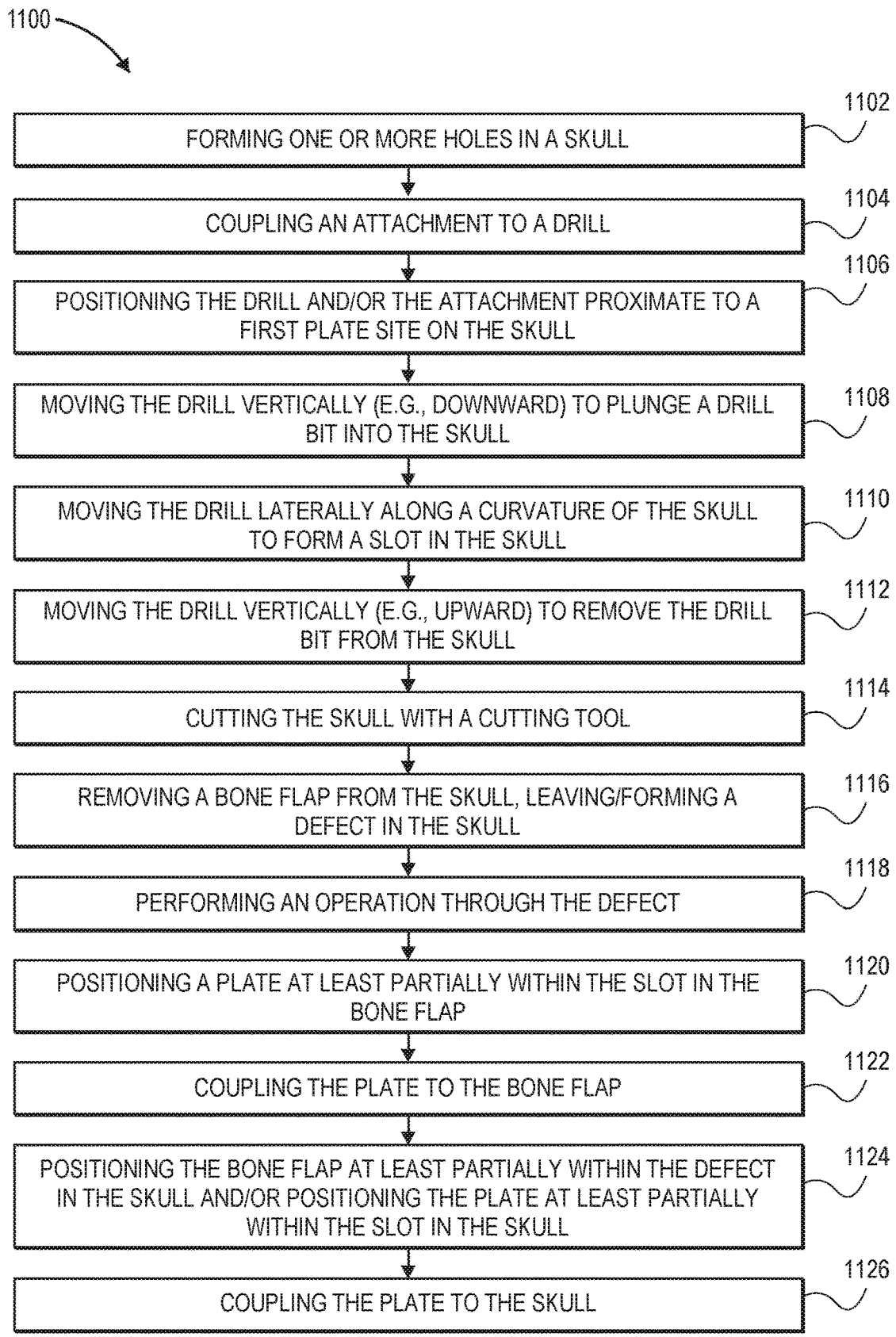
FIG. 11 illustrates a flowchart of a method for performing a surgical procedure (e.g., a craniotomy), according to an embodiment.

FIG. 11 illustrates a flowchart of a method 1100 for performing a surgical procedure (e.g., a craniotomy), according to an embodiment. The method 1100 may create the slot 400 before the bone flap 120 is removed from the skull 100. In the method 1100, the bone flap 120 is re-used. Thus, the implant 120 is not used. An illustrative order of the method 1100 is described below; however, or one or more steps may be performed in a different order, repeated, or omitted.

The method 1100 may include forming one or more (e.g., burr) holes 700 in the skull 100, as at 1102. The method 1100 may also include attaching the attachment 220, 820 to the drill 210, as at 1104. The method 1100 may also include positioning the drill 210 and/or the attachment 220, 820 proximate to a first plate site on the skull 100, as at 1106. As used herein, a plate site refers to a site/location where a plate 130A, 130B will be later placed/coupled during the method 1100. This step may include contacting the skull 100 with the anchoring feature(s) 242 of the outer housing 240, 840 to secure the attachment 220, 820 in place with respect to the skull 100. Method 1100 can also be readily adapted for use with, for example, attachment 1300, or a handheld, non-wall powered device, such as surgical tool 1400.

The method 1100 may also include moving the drill 210 vertically (e.g., downward) to plunge the drill bit 212 into the skull 100, as at 1108. This may include moving drill 210, the drill bit 212, and/or the inner housing 230, 830 downward with respect to the skull 100, the outer housing 240, 840, and/or the guide adapter 250, 850. The vertical movement may be facilitated by the engagement between the guide adapter 250, 850 and the vertical guide 260, 860.

With the drill bit 212 plunged into the skull 100, the method 1100 may also include moving the drill 210 and the attachment 220, 820 laterally (e.g., along a curvature of the skull 100), as at 1110. This may include moving drill 210, the drill bit 212, the inner housing 230, 830, and/or the guide adapter 250, 850 laterally with respect to the skull 100 and/or the outer housing 240, 840. The lateral movement may be facilitated by the engagement between the guide adapter 250, 850 and the horizontal guide 270, 870. The lateral movement may form the slot 400 in the skull 100. More particularly, as described below, the lateral movement may form the first portion 402 of the slot 400 in the bone flap 120 and the second portion 404 of the slot 404 in the remainder of the skull 100 (e.g., outside of the bone flap 120).

The method 1100 may also include moving the drill 210 vertically (e.g., upward) to remove the drill bit 212 from the skull 100, as at 1112. This may include moving drill 210, the drill bit 212, and/or the inner housing 230, 830 upward with respect to the skull 100, the outer housing 240, 840, and/or the guide adapter 250, 850. The vertical movement may be facilitated by the engagement between the guide adapter 250, 850 and the vertical guide 260, 860.

One of more of the steps 1102-1112 may be repeated to form additional slots 400 in the skull 100. The method 1100 may also include cutting the skull 100 with a cutting tool, as at 1114. The cutting may be along a path that extends through the slots 400 and/or the burr holes 700. For example, the path may divide the slots 400 into the first and second portions 402, 404, as shown in FIGS. 7A and 7B.

Once the cutting is complete, the method 1100 may also include removing the bone flap 120 from the skull 100, which forms/leaves the defect 110 in the skull 100, as at 1116. The method 1100 may include performing an operation (e.g., a craniotomy) through the defect 110, as at 1118.

The method 1100 may also include positioning the plate 130A at least partially within the slot 400 in the bone flap 120, as at 1120. This may include positioning the first portion 132A of the plate 130A into the corresponding first portion 402 of the slot 400 in the bone flap 120. As shown in FIG. 4B, the outer surface of the plate 130A may be flush (or recessed) with respect to the outer surface of the bone flap 120.

The method 1100 may also include coupling the plate 130A to the bone flap 120, as at 1122. This may include inserting the screws 140 into/through the plate 130A and the bone flap 120 to couple the plate 130A to the bone flap 120. As shown in FIG. 4B, the outer surfaces of the screws 140 may be flush (or recessed) with respect to the outer surface of the bone flap 120.

The method 1100 may also include positioning the bone flap 120 at least partially within the defect 110 in the skull 100 and/or positioning the plate 130A at least partially within the slot 400 in the skull 100, as at 1124. These two things may happen substantially simultaneously. This step may include positioning the second portion 134A of the plate 130A into the corresponding second portion 404 of the slot 400 in the skull 100. As shown in FIG. 4B, the outer surface of the plate 130A may be flush (or recessed) with respect to the outer surface of the skull 100.

The method 1100 may also include coupling the plate 130A to the skull 100, as at 1126. This may include inserting the screws 140 into/through the plate 130A and the skull 100 to couple the plate 130A to the skull 100. As shown in FIG. 4B, the outer surfaces of the screws 140 may be flush (or recessed) with respect to the outer surface of the skull 100.

Figure 12:
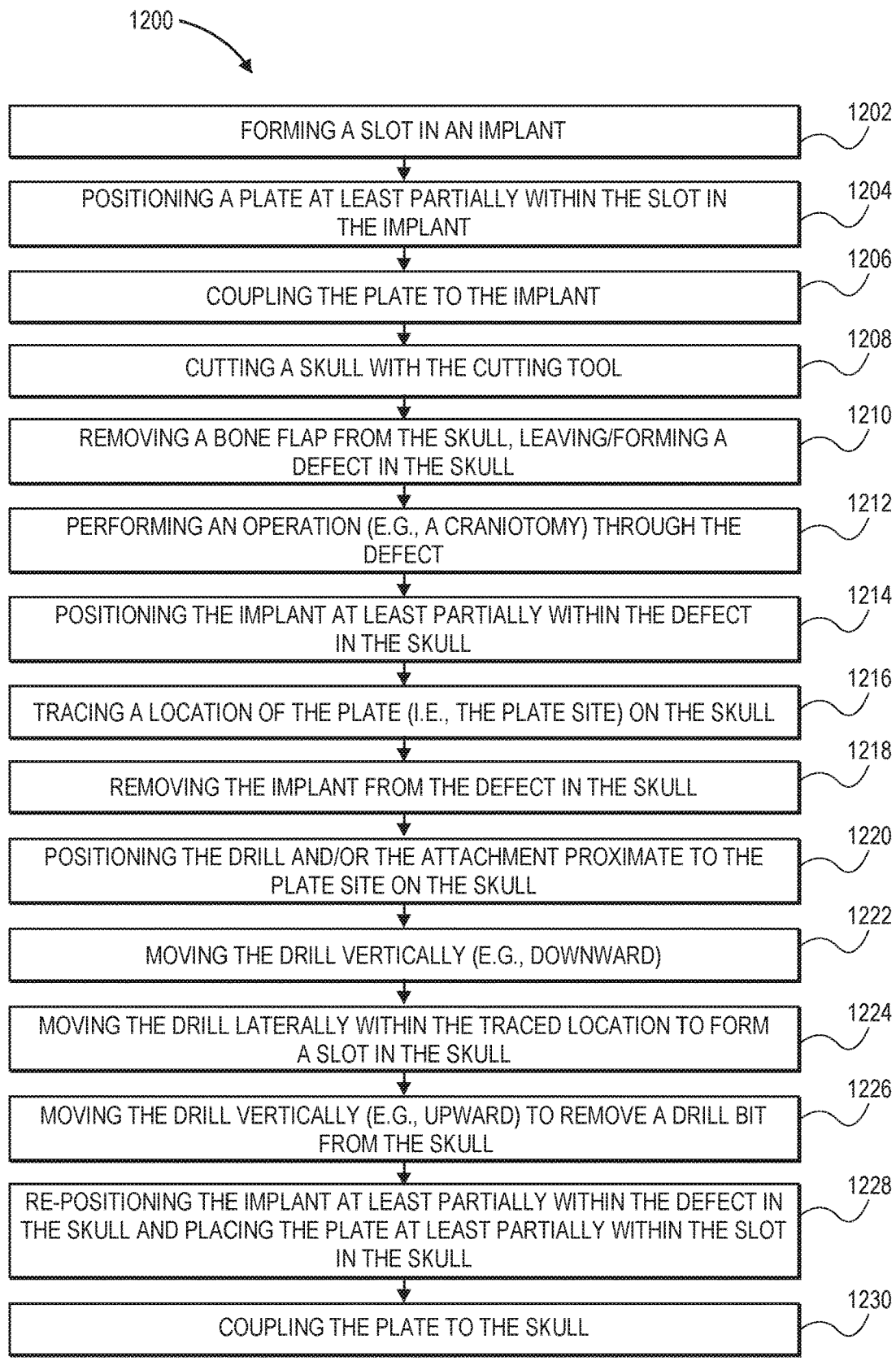
FIG. 12 illustrates a flowchart of another method for performing a surgical procedure (e.g., a craniotomy), according to an embodiment.
Figure 13B:
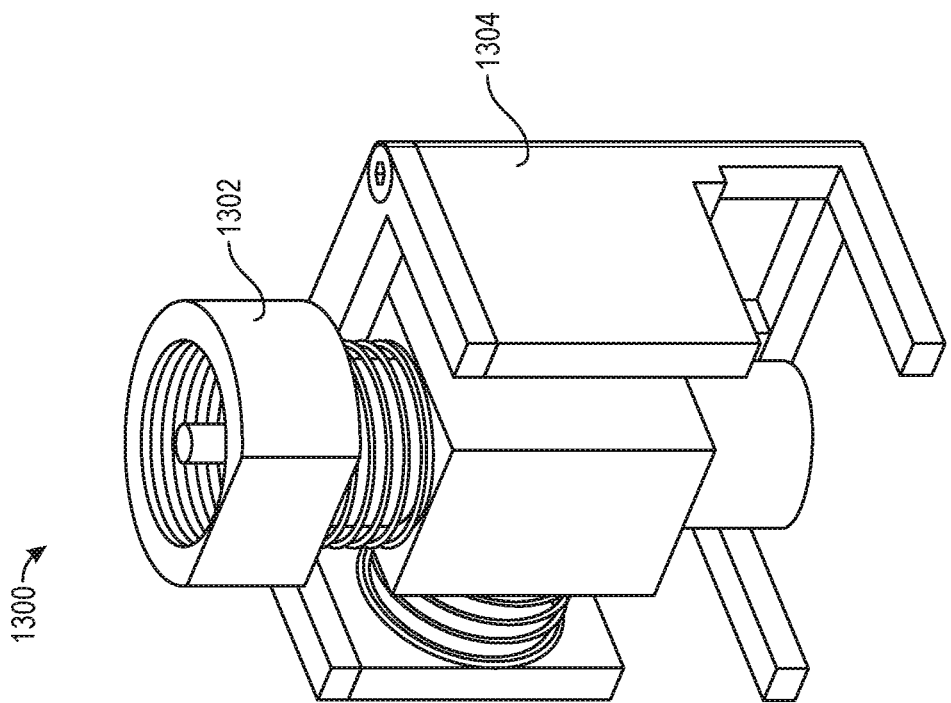
FIG. 13B illustrates a schematic cutaway, perspective view of the attachment depicted in FIG. 13A.
Figure 13A:
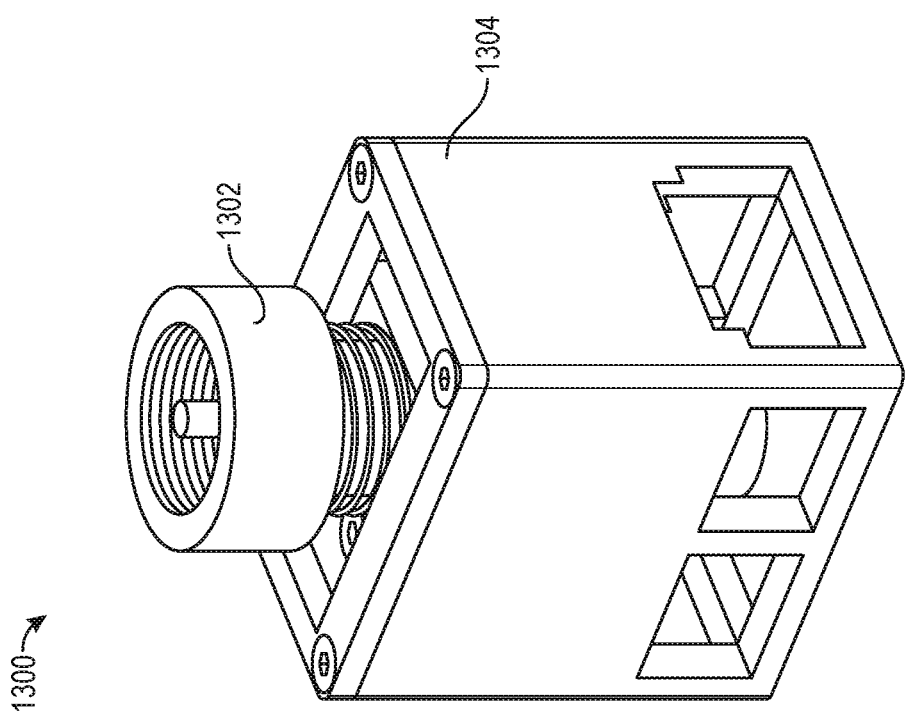
FIG. 13A illustrates a schematic perspective view of an example of another attachment, according to an embodiment.
Figure 13C:
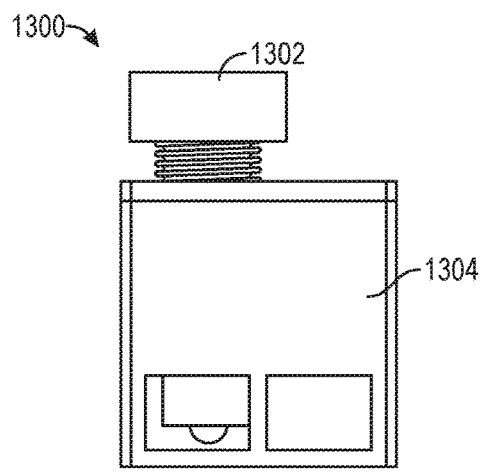
FIG. 13C illustrates a schematic side view of the attachment depicted in FIG. 13A in a first state, according to an embodiment.
Figure 13D:
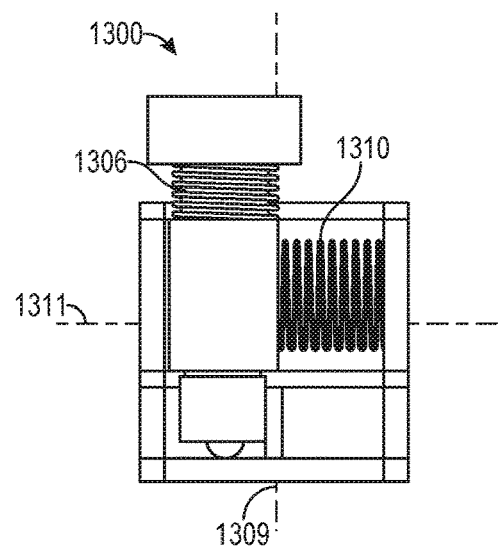
FIG. 13D illustrates a schematic cutaway, side view of the attachment depicted in FIG. 13C.
Figure 13E:
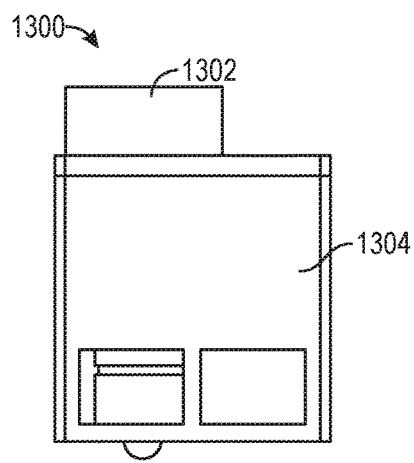
FIG. 13E illustrates a schematic side view of the attachment depicted in FIG. 13A in a second state, according to an embodiment.
Figure 13F:
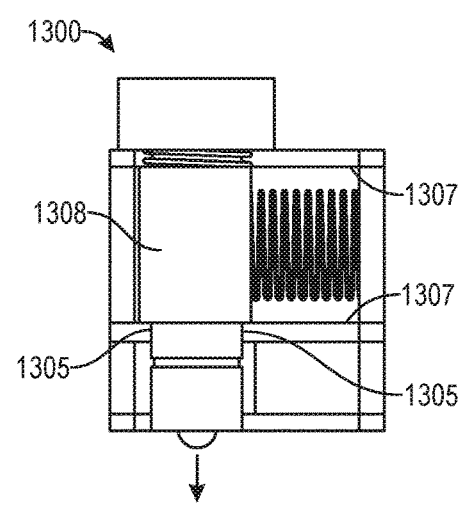
FIG. 13F illustrates a schematic cutaway, side view of the attachment depicted in FIG. 13E.
Figure 13G:
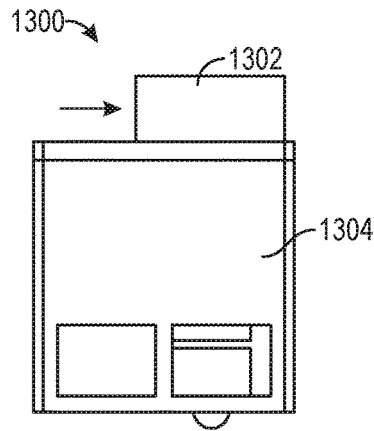
FIG. 13G illustrates a schematic side view of the attachment depicted in FIG. 13A in a third state, according to an embodiment.
Figure 13H:
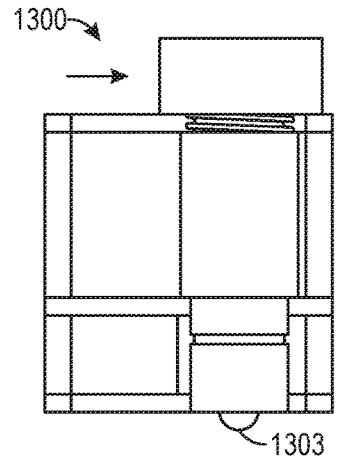
FIG. 13H illustrates a schematic cutaway, side view of the attachment depicted in FIG. 13F.
Figure 14E:
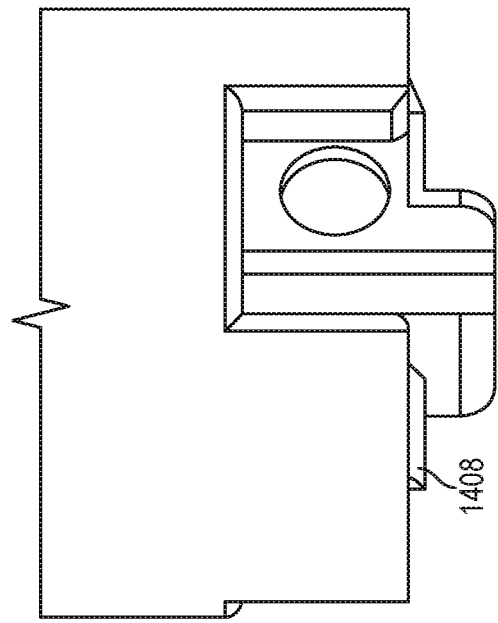
FIG. 14E illustrates another schematic detailed side view of part of a base portion of the surgical tool depicted in FIG. 14A.
Figure 14D:
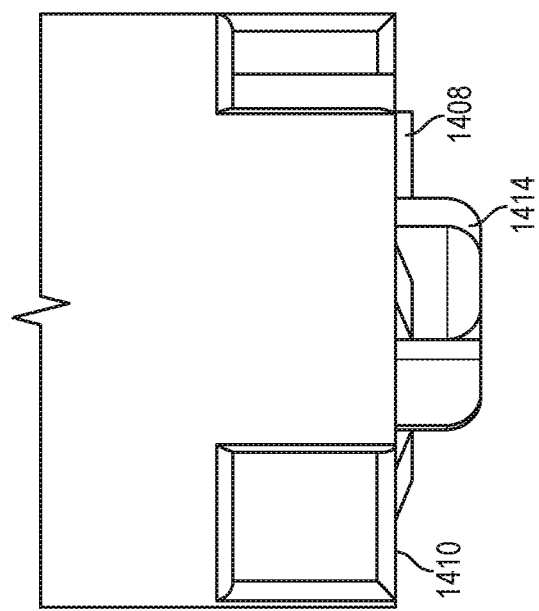
FIG. 14D illustrates a schematic detailed side view of part of a base portion of the surgical tool depicted in FIG. 14A.
Figure 14F:
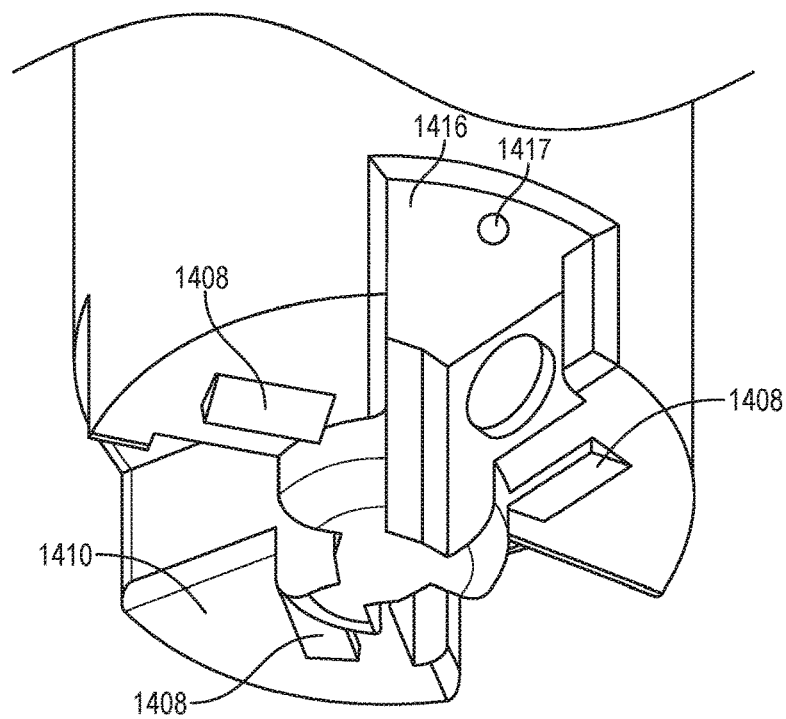
FIG. 14F illustrates a schematic detailed perspective view of part of a base portion of the surgical tool depicted in FIG. 14A.
Figure 14G:
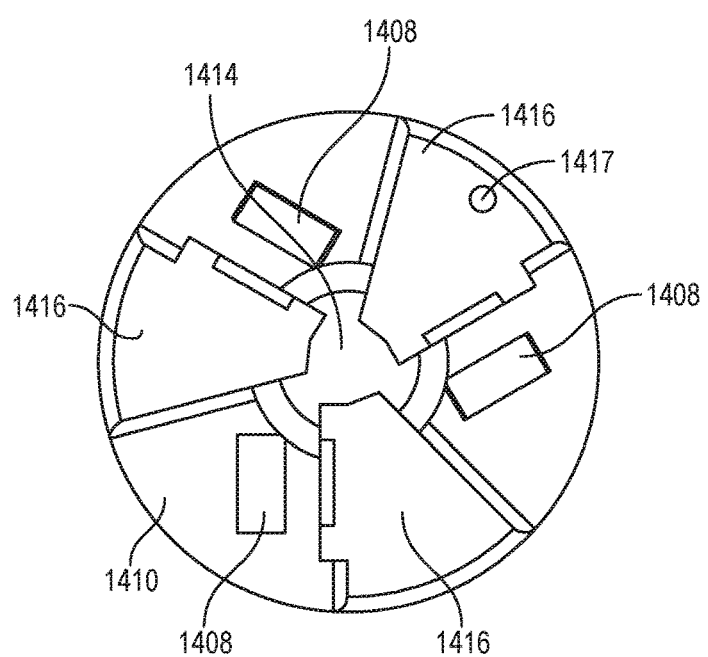
FIG. 14G illustrates a schematic bottom view of the surgical tool depicted in FIG. 14A.

FIG. 12 illustrates a flowchart of another method 1200 for performing a surgical procedure (e.g., a craniotomy), according to an embodiment. The method 1200 may create the slot 400 in the skull 100 after the bone flap 120 is removed from the skull 100. In the method 1200, the bone flap 120 is discarded and replaced with the implant 120. An illustrative order of the method 1200 is described below; however, or one or more steps may be performed in a different order, repeated, or omitted.

The method 1200 may include forming at least a portion of the slot 400 in the implant 120, as at 1202. More particularly, this may include forming the first portion 402 of the slot 400 in the implant 120 using the surgical tool 200. In another embodiment, the implant 120 may be created/formed (e.g., using a 3D printer) with the portion 402 of the slot 400 therein, and the surgical tool 200 may not be needed to form the portion 402 of the slot 400 in the implant 120.

The method 1200 may also include positioning the plate 130A at least partially within the slot 400 in the implant 120, as at 1204. This may include positioning the first portion 132A of the plate 130A into the corresponding first portion 402 of the slot 400 in the implant 120. As shown in FIG. 4B, the outer surface of the plate 130A may be flush (or recessed) with respect to the outer surface of the implant 120.

The method 1200 may also include coupling the plate 130A to the implant 120, as at 1206. This may include inserting the screws 140 into/through the plate 130A and the implant 120 to couple the plate 130A to the implant 120. As shown in FIG. 4B, the outer surfaces of the screws 140 may be flush (or recessed) with respect to the outer surface of the implant 120. One or more of steps 1202-1206 may be repeated to add additional slots and/or plates (e.g., plate 130B) to the implant 120.

The method 1200 may also include cutting the skull 100 with the cutting tool, as at 1208. Once the cutting is complete, the method 1200 may also include removing the bone flap 120 from the skull 100, which forms/leaves the defect 110 in the skull 100, as at 1210. The method 1200 may include performing an operation (e.g., a craniotomy) through the defect 110, as at 1212.

The method 1200 may also include positioning the implant 120 at least partially within the defect 110 in the skull 100, as at 1214. When the implant 120 is positioned at least partially within the defect 110, the method 1200 may also include tracing a location of the plate 130A (i.e., the plate site) on the skull 100 (e.g., using a bone marker), as at 1216. This may include tracing the location of the second portion 134A of the plate 130A on the skull 100. This step may be repeated for additional plates (e.g., plate 130B) that are coupled to the implant 120. The method 1200 may also include removing the implant 120 from the defect 110 in the skull 100, as at 1218.

The method 1200 may also include positioning the drill 210 and/or the attachment 220, 820 proximate to the plate site on the skull 100, as at 1220. This step may include contacting the skull 100 with the anchoring feature(s) 242 of the outer housing 240, 840 to secure the attachment 220, 820 in place with respect to the skull 100.

The method 1200 may also include moving the drill 210 vertically (e.g., downward), as at 1222. This may include moving drill 210, the drill bit 212, and/or the inner housing 230, 830 downward with respect to the skull 100, the outer housing 240, 840, and/or the guide adapter 250, 850. The vertical movement may be facilitated by the engagement between the guide adapter 250, 850 and the vertical guide 260, 860. In at least one embodiment, moving the drill 210 vertically downward may plunge the drill bit 212 into the traced location on the skull 100. In another embodiment, moving the drill 210 vertically downward may move the drill bit 212 into the defect 110, proximate to the traced location.

The method 1200 may also include moving the drill 212 laterally within the traced location, as at 1224. This may include moving drill 210, the drill bit 212, the inner housing 230, 830, and/or the guide adapter 250, 850 laterally with respect to the skull 100 and/or the outer housing 240, 840. The lateral movement may be facilitated by the engagement between the guide adapter 250, 850 and the horizontal guide 270, 870. The lateral movement may form the slot 400 in the skull 100. More particularly, the lateral movement may form the second portion 404 of the slot 400 in the skull 100 within the traced location.

In another embodiment, moving the drill 212 laterally within the traced location may include rocking the attachment 820. More particularly, the attachment 820 may be positioned such that the edge 844 of the outer housing 840 contacts/abuts the edge of the skull 100 that defines the defect 110. Then, the drill 210 and the inner housing 830 may move laterally within the traced location while the outer housing 840 rocks, as shown in FIG. 10.

The method 1200 may also include moving the drill 210 vertically (e.g., upward) to remove the drill bit 212 from the skull 100, as at 1226. This may include moving drill 210, the drill bit 212, and/or the inner housing 230, 830 upward with respect to the skull 100, the outer housing 240, 840, and/or the guide adapter 250, 850. The vertical movement may be facilitated by the engagement between the guide adapter 250, 850 and the vertical guide 260, 860. Steps 1220-1226 may be repeated for each plate site.

The method 1200 may also include re-positioning the implant 120 at least partially within the defect 110 in the skull 100, as at 1228. This may include positioning the plate 130A into the slot that was just created in the skull 100. More particularly, this may include positioning the second portion 134A of the plate 130A into the corresponding second portion 404 of the slot 400 in the skull 100.

The method 1200 may also include coupling the plate 130A to the skull 100, as at 1230. This may include inserting the screws 140 into/through the plate 130A and the skull 100 to couple the plate 130A to the skull 100. As shown in FIG. 4B, the outer surfaces of the plate 130A and screws 140 may be flush (or recessed) with respect to the outer surface of the skull 100.

Figure 15:
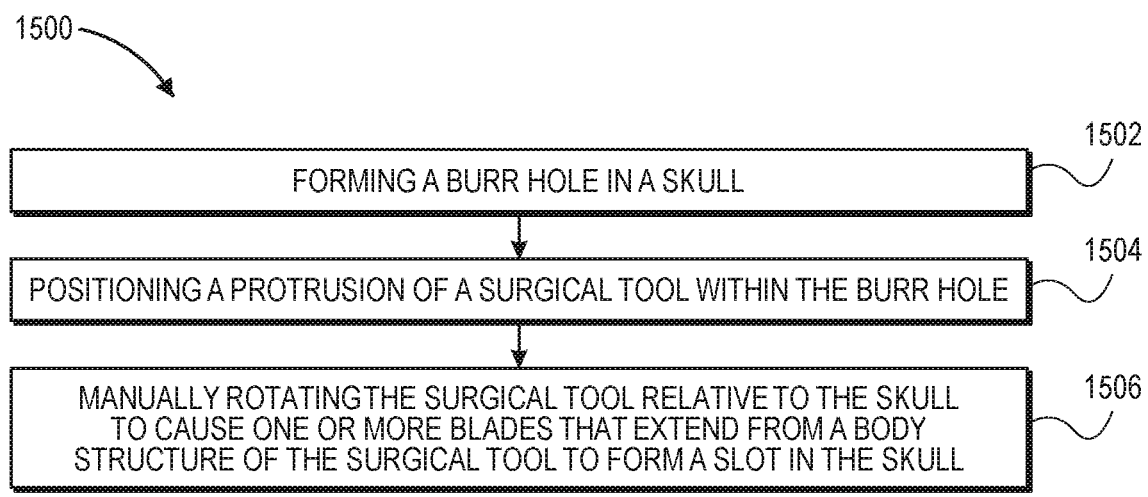
FIG. 15 illustrates a flowchart of a method for performing a surgical procedure (e.g., a craniotomy), according to an embodiment.

FIG. 15 illustrates a flowchart of a method 1500 for performing a surgical procedure (e.g., a craniotomy), according to an embodiment. The method 1500 includes forming a burr hole, as at 1502. The method 1500 also includes positioning a protrusion of a surgical tool (e.g., a handheld, non-wall powered device, such as surgical tool 1400) within the burr hole, as at 1504. In addition, the method 1500 also includes manually rotating the surgical tool relative to the skull to cause one or more blades that extend from a body structure of the surgical tool to form a slot in the skull, as at 1506.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A surgical tool, comprising:
   a drill comprising a drill bit; and
   an attachment configured to be coupled to the drill, wherein the attachment comprises:
      an inner housing defining a bore, wherein the drill is configured to extend through the bore such that the drill bit extends vertically-below a lower end of the inner housing by a predetermined amount;
      an outer housing positioned at least partially around the inner housing, wherein a lower end of the outer housing comprises an anchoring feature;
      a vertical guide coupled to or integral with the inner housing;
      a horizontal guide coupled to or integral with the outer housing; and
      a guide adapter slidingly engaged with the vertical guide and the horizontal guide, wherein the guide adapter is configured to slide vertically along the vertical guide when the drill and the inner housing move vertically with respect to the outer housing, and wherein the guide adapter is configured to slide horizontally along the horizontal guide when the drill and the inner housing move horizontally with respect to the outer housing.

2. The surgical tool of claim 1, wherein the drill and the inner housing are configured to move vertically with respect to the outer housing from a first state to a second state, wherein the drill bit does not extend vertically-below the lower end of the outer housing in the first state, and wherein the drill bit extends vertically-below the lower end of the outer housing in the second state.

3. The surgical tool of claim 2, wherein the drill bit is configured to plunge into a skull when the drill bit extends vertically-below the lower end of the outer housing, and wherein the drill bit is configured to form a slot in the skull when the drill and the inner housing move horizontally with respect to the outer housing.

4. The surgical tool of claim 1, wherein the inner housing is configured to pivot with respect to the outer housing from a first state to a second state, wherein a central longitudinal axis through the inner housing is substantially parallel with a central longitudinal axis through the outer housing in the first state.

5. The surgical tool of claim 4, wherein an angle between the central longitudinal axis through the inner housing and the central longitudinal axis through the outer housing is from 5° to 45° in the second state.

6. The surgical tool of claim 5, wherein the outer housing defines a window formed proximate to a lower end of the outer housing.

7. The surgical tool of claim 6, wherein the window extends from 25% to 75% around a perimeter of the outer housing, and wherein the inner housing is configured to extend at least partially through the window in the second state.

8. An attachment for a drill, the attachment comprising:
an inner housing configured to be coupled to the drill and defining a bore, wherein the drill is configured to extend through the bore such that a drill bit of the drill extends vertically-below a lower end of the inner housing by a predetermined amount;
an outer housing positioned at least partially around the inner housing,
a vertical guide coupled to or integral with the inner housing;
a horizontal guide coupled to or integral with the outer housing;
a guide adapter slidingly engaged with the vertical guide and the horizontal guide, wherein the inner housing and the vertical guide are configured to slide vertically relative to the guide adapter when the drill and the inner housing move vertically with respect to the outer housing, and wherein the guide adapter is configured to slide horizontally along the horizontal guide when the drill and the inner housing move horizontally with respect to the outer housing;
a vertical resilient coupling operably engaged with the inner housing and the guide adapter, wherein the vertical resilient coupling is configured to resiliently couple the inner housing and the drill with the guide adapter along a vertical axis when the inner housing and the drill move vertically with respect to the outer housing; and,
a horizontal resilient coupling operably engaged with the guide adapter and the outer housing, wherein the horizontal resilient coupling is configured to resiliently couple the guide adapter with the outer housing along a horizontal axis when the inner housing and the drill move horizontally with respect to the outer housing.

9. The attachment of claim 8, wherein the drill bit does not extend vertically-below a lower end of the outer housing when the attachment is in a first state, and wherein the drill bit extends vertically-below the lower end of the outer housing when the attachment is in a second state.

10. The attachment of claim 8, wherein the inner housing is configured to pivot with respect to the outer housing from a first state to a second state, and wherein a central longitudinal axis through the inner housing is substantially parallel with a central longitudinal axis through the outer housing in the first state.

11. The attachment of claim 10, wherein an angle between the central longitudinal axis through the inner housing and the central longitudinal axis through the outer housing is from 5° to 45° in the second state.

12. The attachment of claim 8, wherein the outer housing defines a window formed proximate to a lower end of the outer housing.

13. The attachment of claim 8, wherein the vertical and horizontal resilient couplings independently comprise a spring, an elastomeric material, and a hydraulic piston.

14. The attachment of claim 8, wherein the attachment is configured to remove biological material from a skull of a subject to create an inset of a selected depth in the skull.

15. The surgical tool of claim 14, wherein the inset comprises a cross-sectional shape selected from the group consisting of: a circle, an oval, a square, a rectangle, and a triangle.

16. A method for performing a surgical procedure, the method comprising:
contacting a skull with an outer housing of a surgical tool, wherein the surgical tool comprises an inner housing, the outer housing, and a drill that comprises a drill bit;
moving the drill and the inner housing downward with respect to the outer housing and the skull; and
moving the drill and the inner housing laterally with respect to the outer housing and the skull to cause the drill bit to form a slot in the skull.

17. The method of claim 16, further comprising:
cutting the skull to form a bone flap, wherein a first portion of the slot is formed in the bone flap, and a second portion of the slot is formed in a remainder of the skull;
removing the bone flap to form a defect in the skull;
positioning a first portion of a plate within the first portion of the slot; and
coupling the first portion of the plate to the bone flap using a first coupling member, wherein an outer surface of the plate and an outer surface of the first coupling member are flush with, or recessed with respect to, an outer surface of the bone flap.

18. The method of claim 17, further comprising:
positioning the bone flap back into the defect;
positioning a second portion of the plate within the second portion of the slot; and
coupling the second portion of the plate to the remainder of the skull using a second coupling member, wherein the outer surface of the plate and an outer surface of the second coupling member are flush with, or recessed with respect to, an outer surface of the remainder of the skull.

19. The method of claim 16, further comprising:
positioning a first portion of a plate within a slot formed in an implant;
coupling the first portion of the plate to the implant using a first coupling member, wherein an outer surface of the plate and an outer surface of the first coupling member are flush with, or recessed with respect to, an outer surface of the implant;
cutting the skull to form a bone flap;
removing the bone flap to form a defect in the skull; and
positioning the implant at least partially within the defect in the skull.

20. The method of claim 19, further comprising:
tracing a location of a second portion of the plate in the skull;
removing the implant from the defect in the skull prior to forming the slot in the skull, wherein the drill and the inner housing are moved laterally with respect to the outer housing and the skull to cause the drill bit to form the slot in the traced location on the skull;

re-positioning the implant at least partially within the defect in the skull after the slot is formed in the skull, wherein re-positioning the implant comprises positioning a second portion of the plate within the slot in the skull; and coupling the second portion of the plate to the skull using a second coupling member, wherein the outer surface of the plate and an outer surface of the second coupling member are flush with, or recessed with respect to, an outer surface of the skull.

* * * * *